US008614203B2

(12) United States Patent
Stein et al.

(10) Patent No.: US 8,614,203 B2
(45) Date of Patent: *Dec. 24, 2013

(54) METHODS FOR THE TREATMENT OF A CENTRAL NERVOUS SYSTEM INJURY VIA A TAPERED ADMINISTRATION PROTOCOL

(75) Inventors: Donald G. Stein, Atlanta, GA (US); Sarah Cutler, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/550,148

(22) Filed: Jul. 16, 2012

(65) Prior Publication Data

US 2012/0289491 A1   Nov. 15, 2012

Related U.S. Application Data

(63) Continuation of application No. 11/909,276, filed as application No. PCT/US2006/010984 on Mar. 24, 2006, now abandoned.

(60) Provisional application No. 60/664,728, filed on Mar. 24, 2005, provisional application No. 60/729,663, filed on Oct. 24, 2005.

(51) Int. Cl.
*A61K 31/56* (2006.01)

(52) U.S. Cl.
USPC ........................................................ 514/177

(58) Field of Classification Search
USPC ........................................................ 514/177
See application file for complete search history.

(56) References Cited

U.S. PATENT DOCUMENTS

| | | | |
|---|---|---|---|
| 4,404,366 A | 9/1983 | Boguslaski et al. |
| 5,120,723 A | 6/1992 | Gee et al. |
| 5,206,415 A | 4/1993 | Covey et al. |
| 5,212,167 A | 5/1993 | Farb |
| 5,232,917 A | 8/1993 | Bolger et al. |
| 5,292,906 A | 3/1994 | Covey et al. |
| 5,344,826 A | 9/1994 | Covey et al. |
| 5,366,968 A | 11/1994 | Farb |
| 5,550,120 A | 8/1996 | Jackson |
| RE35,517 E | 5/1997 | Gee et al. |
| 5,633,011 A | 5/1997 | Dong et al. |
| 5,728,688 A | 3/1998 | Labrie |
| 5,763,431 A | 6/1998 | Jackson |
| 5,763,492 A | 6/1998 | Johnson et al. |
| 5,767,117 A | 6/1998 | Moskowitz |
| 5,780,460 A | 7/1998 | Labrie |
| 5,798,347 A | 8/1998 | Labrie |
| 5,807,849 A | 9/1998 | Labrie |
| 5,824,671 A | 10/1998 | Labrie |
| 5,837,544 A | 11/1998 | Capon et al. |
| 5,837,700 A | 11/1998 | Labrie |
| 5,843,932 A | 12/1998 | Labrie |
| 5,872,114 A | 2/1999 | Labrie |
| 5,888,996 A | 3/1999 | Farb |
| 5,922,700 A | 7/1999 | Labrie |
| 5,925,630 A | 7/1999 | Upasani et al. |
| 5,929,061 A | 7/1999 | Moskowitz |
| 5,939,545 A | 8/1999 | Upasani et al. |
| 5,942,241 A | 8/1999 | Chasin et al. |
| 5,955,455 A | 9/1999 | Labrie |
| 6,114,388 A | 9/2000 | Geffard |
| 6,245,757 B1 | 6/2001 | Chopp et al. |
| 7,473,687 B2 | 1/2009 | Hoffman et al. |
| 7,915,244 B2 | 3/2011 | Hoffman et al. |
| 2001/0001280 A1 | 5/2001 | Dong et al. |
| 2008/0318914 A1 | 12/2008 | Hoffman et al. |
| 2009/0325920 A1 | 12/2009 | Hoffman et al. |
| 2011/0224181 A1 | 9/2011 | Hoffman et al. |

FOREIGN PATENT DOCUMENTS

| | | |
|---|---|---|
| WO | WO 89/02272 | 3/1989 |
| WO | WO 94/23708 | 10/1994 |
| WO | WO 97/43989 | 11/1997 |
| WO | WO 98/50042 | 11/1998 |

OTHER PUBLICATIONS

Goss et. al. (Pharmacology, Biochemistry and Behavior (2003) 76:231-242).*
Shear et. al. (Experimental Neurology (2002) 178:59-67).*
Smith (Steroids (2002) 67: 519-528).*
Hajj-Ali et. al. (Critical Care Clinics (2002) 18:897-914).*
Reder et. al. (Neurology (1994) 44:2289-2294).*
Adams et. al. (Progress in Transplantation (2001) 11:217-223).*
Notice of Allowance issued on Aug. 11, 2008, by the Examiner in U.S. Appl. No. 11/527,816 (US 7,473,687).
Notice of Allowance issued on Feb. 8, 2008, by the Examiner in U.S. Appl. No. 11/527,816 (US 7,473,687).
Office Action issued on May 3, 2007, by the Examiner in U.S. Appl. No. 11/527,816 (US 7,473,687).
Office Action issued on Aug. 19, 2009, by the Examiner in U.S. Appl. No. 12/117,217 (US 2008/0318914).
U.S. Appl. No. 13/045,180, filed Apr. 24, 2012, Hoffman et al.
International Search Report issued on Nov. 14, 2006 for application No. PCT/US2006/010984 (corresponding to US 2009/0221544).

(Continued)

*Primary Examiner* — Marcos Sznaidman
(74) *Attorney, Agent, or Firm* — Foley & Lardner LLP

(57) ABSTRACT

The present invention provides methods for the treatment or the prevention of neuronal damage in the CNS. Specifically, the methods of the invention provide for the administration of a therapeutically effective amount of a progestin or progestin metabolite following a traumatic or ischemic injury to the CNS such that, prior to termination of administration of the progestin or progestin metabolite the administration is tapered to avoid withdrawal. The drug taper employed can involve a linear taper, an exponential taper, progressively dividing administered doses by 50%, or can be determined based on the treating physician's assessment of the patient's response to therapy. The tapered administration methods of the present invention may be used in combination with any therapeutic protocol or regimen for the administration of a therapeutically effective amount of a progestin or progestin metabolite to treat a traumatic or ischemic CNS injury.

18 Claims, 10 Drawing Sheets

(56) References Cited

OTHER PUBLICATIONS

International Search Report issued on Mar. 25, 2008 for application No. PCT/US2007/079655 (corresponding to US 7,473,687).
International Search Report issued on Nov. 14, 2006 for application No. PCT/US2006/010797 (Corresponding to US 2009/0325920).
Wright et al., "Steady-State Serum Concentrations of Progesterone Following Continuous Intravenous Infusion in Patients with Acute Moderate to Severe Traumatic Brain Injury," *J. Clin. Pharmacol.*, vol. 45, pp. 640-648 (2005).
Cutler et al., "Slow-Release and injected progesterone treatments enhance acute recovery after traumatic brain injury," *Pharmacology, Biochemistry and Behavior*, vol. 84, No. 3, pp. 420-428 (2006).
Cutler et al., "Tapered progesterone withdrawal promotes long-term recovery following brain trauma," *Experimental Neurology*, vol. 200, No. 2, pp. 378-385, Aug. 2006.
Cutler et al., "Tapered progesterone withdrawal enhances behavioral and molecular recover after traumatic brain injury," *Experimental Neurology*, vol. 195, No. 2, pp. 423-429 (Oct. 2005).
Guo et al., "Progesterone administration modulates AQP4 expression and edema after traumatic brain injury in male rats," *Experimental Neurology*, vol. 198, No. 2, pp. 469-478 (2006).
He et al., "Progesterone and allopregnanolone reduce inflammatory cytokines after traumatic brain injury," *Experimental Neurology*, vol. 189, No. 2, pp. 404-412 (2004).
Jones et al., "The neuroprotective effect of progesterone after traumatic brain injury in male mice is independent of both the inflammatory response and growth factor expression," *Euro Journal of Neuroscience*, vol. 21, No. 6, pp. 1547-1554 (2005).
O'Connor et al., "Both estrogen and progesterone attenuate edema formation following diffuse traumatic brain injury in rats," *Brain Research*, vol. 1062, No. 102, pp. 171-174 (2005).
Goss et al., "Behavioral effects and anatomic correlates after brain injury: A progesterone dose-response study," *Pharmacology, Biochemistry and Behavior*, vol. 76, No. 2, pp. 231-242, Sep. 2003.
Shear et al., "Progesterone protects against necrotic damage and behavioral abnormalities caused by traumatic brain injury," *Experimental Neurology*, vol. 178, No. 1, Nov. 2002.
Roberts et al., "Absence of evidence for the effectiveness of five interventions routinely used in the intensive care management of severe heads injury: a systematic review," *J. Neurol. Neurosurg. Psychiatry*, vol. 65, pp. 729-733, 1998.
Vink et al., "An overview of new and novel pharmacothereapies for use in traumatic brain injury," *Clinical and Experimental Pharmacology and Physiology*, vol. 28, pp. 919-921, 2001.
Faden et al., "Neuroprotection and traumatic brain injury: theoretical option or realistic proposition," *Curr. Opin. Neurol.*, vol. 15, pp. 707-712, 2002.
Narayan et al., "Clinical trials in head injury," *J. Neurotrauma*, vol. 19, No. 5, pp. 503-557, 2002.
Matz, "Clinical Trials for Traumatic Brain Injury: The road traveled and development of new pathways," *Seminars in Neurosurgery*, vol. 14, No. 2, pp. 139-146, 2003.
Doppenberg et al., "Clinical Trials in Traumatic Brain Injury: Lessons for the Future," *J. Neurosurg. Anesthesiol*, vol. 16, No. 1, pp. 87-94, 2004.
Tolias et al., "Critical Appraisal of Neuroprotection Trials in Head Injury: What Have We Learned?," *NeuroRx®*, vol. 1, pp. 71-79, 2004.
Tse et al., "Cerebral protection in traumatic brain injury," *Surgical Practice*, vol. 9, pp. 122-125, 2005.
Maas et al., "Prognosis and Clinical Trial Desin in Traumatic Brain Injury: The IMPACT Study," *J. Neurotrauma*, vol. 24, No. 2, pp. 232-238, 2007.
Stein et al., "Does Progesterone Have Neuroprotective Properties?," *Annals of Emergency Medicine*, pp. 1-9, 2007.
Povlishock et al., "Workshop on Animal Models of Traumatic Brain Injury," *J. Neurotrauma*, vol. 11, No. 6, pp. 723-732, 1994.
Laurer et al., "Experimental models of brain trauma," *European J. Head Trauma*, vol. 3, pp. 95-110, 2000.
Finnie, "Animal models of traumatic brain injury: a review," *Aust. Vet. J.*, pp. 628-633, 2001.
Leker et al., "Experimental Models of Head Trauma," *Acta Neurochir.*, vol. 83, pp. 49-54, 2002.
Allolio et al., "High-Dose Progesterone Infusion in Healthy Males: Evidence Against Antiglucocorticord Activity of Progesterone," *European J. Endocrin.*, vol. 133, pp. 696-700, 1995.
Bender et al., Effect of Benzodiazepines and Neurosteroids on Ammonia-Induced Swelling in Cultured Astrocytes, *J. Neurosci. Res.*, vol. 54, pp. 673-680, 1998.
Canonaco et al., "Steroid Hormones and Receptors of the $GABA_A$ Supromolecular Complex," *Neuroendocrinology*, vol. 57, pp. 974-984, 1993.
Celotti et al., "The 5α-Reductase in the Brain: Molecular Aspects and Relation to Brain Function," *Frontiers in Neuroendocrinology*, vol. 13, No. 2, pp. 163-215, 1992.
Cervantes et al., "Brain Injury Following Cardiorespiratory Arrest in Cats, Effects of Alphaxolone-Alphadolone," *Bol. Estud. Med. Biol.*, vol. 37, pp. 17-27, 1989.
Chen et al., "Neuroprotective Effects of Progesterone After Transient Middle Cerebral Artery Occlusion," *J. Neurol. Sci.*, vol. 171, pp. 24-30, 1999.
Djebaili et al., "Allopregnanolone and Progesterone Decrease Cell Death and Cognitive Deficits After a Contusion of the Rat Pre-Frontal Cortex," *Neuroscience*, vol. 123, pp. 349-359, 2004.
Djebaili et al., "The Neurosteroids Progesterone and Allopregnanolone Reduce Cell Death, Gliosis, and Functional Deficits After Traumatic Brain Injury in Rats," *J. Neurotrauma*, vol. 2, pp. 106-118, 2005.
Fleming et al., "Megestrol Acetate Reverses Multidrug Resistance and Interacts with P-glycoprotein," *Cancer Chemother. Pharmacol.*, vol. 29, pp. 445-449, 1992.
Gee, "Steroid Modulation of the GABA/Benzodiazepine Receptor-Linked Chloride Ionophore," *Molecular Neurobiology*, vol. 2, pp. 291-317, 1998.
Ghezzi et al., "Neurosteroid Levels are Increased in vivo after LPS Treatment and Negatively Regulater LPS-induced TNF Productions," *European Cytokine Network*, 2000, vol. 11, No. 3, pp. 464-469.
Grossman et al., "Effects of Progesterone on the Inflammatory Response to Brain Injury in the Rat," *Brain Res.*, vol. 1008, pp. 29-39, 2004.
Hawkinson et al., "Substituted 3β-Phenylethynyl Derivative of 3α-Hydroxy-5α-pregnan-20-one: Remarkably Potent Neuroactive Steroid Modulators of y-Aminobutyric Acid Receptors," *J. Pharmacology and Experimental Therapies*, vol. 287, No. 1, pp. 198-207, 1998.
He et al., "Alopregnanolone Facilitates Spatial Learning After Traumatic Brain Injury," *Soc. Neurosci. Abstr.*, vol. 26, p. 2296, 2000.
Hoffman et al., "Alopregnanolone Reduces Edema After Controlled Cortical Impact Injury in Rats," *Soc. Neurosci. Abstr.*, vol. 26, p. 967, 2000.
Jiang et al., "Progesterone is Neuroprotective after Transient Middle Cerebral Artery Occulusion in Male Rats," *Brain Research*, vol. 735, pp. 101-107, 1996.
Lambert et al., "Neurosteroid Modulatin of Native and Recombinant $GABA_A$ Receptors," *Cellular and Molecular Neurobiology*, vol. 16, No. 2, pp. 155-174, 1996.
Limmroth et al., "$GABA_A$ -Receptor-Mediated Effects of Progesterone, Its Ring-A-Reduced Metabolites and Synthetic Neuroactive Steroids on Neurogenic Oedema in the Rat Meniges," *British Journal of Pharmacology*, vol. 117, pp. 99-104, 1996.
Maurice et al., "Neuroactive Neurosteroids as Engongenous Effectors for the Sigma1($\alpha_1$) Receptor: Pharmacological Evidence and Therapeutic Opportunities," *Jpn. J. Pharmacol.*, vol. 81, pp. 125-155, 1999.
Melcangi et al., "Steroid Metabolism and Effects in Central and Peripheral Glial Cells," *J. Neurobiol.*, vol. 40, pp. 471-483, 1999.
Michaels, "Cognitive Rehabilitation Advanced by Multifaceted Research, Conference Told," *Can. Med. Assoc. J.*, vol. 153, pp. 465-467, 1995.
Monaghan et al., "Initial Human Experience with Ganaxolone, A Neuroactive Steroid with Antiepileptic Activity," *Epilepsia*, vol. 38, No. 9, pp. 1026-1031, 1997.

(56) References Cited

OTHER PUBLICATIONS

Roof et al., "Progesterone Metabolites May Mediate its Neuroprotective Effects After Traumatic Brain Injury," *J. Neurotrauma*, vol. 14, No. 12, p. 760, 1997.
Roof et al., "Gender Differences in Acute CNS Trauma and Stroke: Neuro-protective Effects of Estrogen and Progesterone," *J. Neurotrauma*, vol. 17, pp. 367-388, 2000.
Roof et al., "Progesterone Treatment Attenuates Brain Edema Following Contusion Injury in Male and Female Rats," *Restorative Neurology and Neuroscience*, vol. 4, pp. 425-427, 1992.
Roof et al., "Progesterone Facilitates Cognitive Recovery and Reduces Secondary Neuronal Loss Caused by Cortical Contusion Injury in Male Rats," *Experimental Neurology*, vol. 129, pp. 64-69, 1994.
Roof et al., "Progesterone Protects Against Lipid Peroxidation Following Traumatic Brain Injury in Rats," *Molecular and Chemical Neuropathology*, vol. 31, pp. 1-11, 1997.
Roof et al., "Progesterone Rapidly Decrease Brain Edema: Treatment Delayed up to 24 Hours is Still Effective," *Experimental Neurology*, vol. 138, pp. 246-251, 1996.
Rupprecht et al., "Steroid Receptor-Mediated Effects of Neuroactive Steroids: Characterization of Structure-Activity Relationship," *Eur. J. of Pharmacology*, vol. 303, pp. 227-234, 1996.
Ströhle et al., "Concentration of 3α-Reduced Neuroactive Steroids and Their Precursors in Plasma of Patients with Major Depression and after Clinical Recovery," *So. of Biol. Psychiatry*, vol. 45, pp. 274-277, 1999.
Taubøll et al., "The effect of Progesterone and its Metabolite 5α-pregnan-3 α-ol-20-one on Focal Epileptic Seizures in the Cat's Visual Vortex in vivo," *Epilepsy Research*, vol. 14, pp. 17-30, 1993.
Weaver et al., "Neuroprotective Activity of a New Class of Steroidal Inhibitors of the N-methyl-D-aspartate Receptor," *Proc. Natl. Acad. Sci., USA*, vol. 94, pp. 1045-10454, 1997.
Wright et al., "Serum Progesterone Levels Correlate with Decreased Cerebral edema After Traumatic Brain Injury in Male Rats," *J. Neurotrauma*, vol. 18, pp. 901-909, 2001.
Yu et al., "Down-Regulation of the GABA Receptor Subunits mRNA levels in Mammalian Cultured Cortical Neurons Following Chronic Neurosteroid Treatment," *Molecular Brain Research*, vol. 41, pp. 163-168, 1996.
Office Action issued on Nov. 22, 2011 by the Examiner in U.S. Appl. No. 13/045,180 (US 2011/0224181).
Office Action issued on Aug. 1, 2011 by the Examiner in U.S. Appl. No. 11/909,278 (US 2009/0325920).
Atsumi et al., "Explanation to Patients about Psychosomatic Disease and Neurosis," Yakkyoku, vol. 50, No. 1, pp. 110-121, 1999.
Miyazaki et al., "Angina Pectoris," The Journal of Therapy, vol. 78, Extra Issue, pp. 591-594, 1996.
Ozaki et al., "Basic research for psychological dependence on morphine under chronic pain," Nippon Rinsho, vol. 59, No. 9, pp. 1704-1712, 2001.
Notice of Allowance issued on Nov. 26, 2010 by the Examiner in U.S. Appl. No. 12/117,217 (US 7,915,244).
Office Action issued on Jul. 22, 2010 by the Examiner in U.S. Appl. No. 12/117,217 (US 7,915,244).
Office Action issued on Mar. 16, 2010 by the Examiner in U.S. Appl. No. 12/117,217 (US 2008/0318914).
Adams et al., "Steroid withdrawal in liver transplant recipients," *Progress in Transplantation*, vol. 11, No. 3, Sep. 2001.
He et al., "Allopregnanolone, a progesterone metabolite, enhances behavioral recovery and decreases neuronal loss after traumatic brain injury," *Restorative Neurology and Neuroscience*, vol. 22, pp. 19-31, 2004.
Stein et al., "Estrogen and progesterone as neuroprotective agents in the treatment of acute brain injuries," *Pediatric Rehabilitation*, vol. 6, No. 1, pp. 13-22, 2003.
Vink et al., "Recent advances in the development of multifactorial therapies for the treatment of traumatic brain injury," *Expert Opin. Investig. Drugs*, vol. 13, No. 10, pp. 1263-1274, 2004.
Wlodarczyk et al., "Steroid withdrawal at 3 months after kidney transplantation: a comparison of two tacrolimus-based regimens," *Transplant International*, vol. 18, pp. 157-162, 2005.
Foldvary-Schaefer et al., "Hormones and seizures," *Cleveland Clinic Journal of Medicine*, vol. 71, Supplement 2, pp. S11-S18, Feb. 2004.
Gulinello et al., "Sex differences in anxiety, sensorimotor gating and expression of the α4 subunit of the $GABA_A$ receptor in the amygdale after progesterone withdrawal," *European Journal of Neuroscience*, vol. 17, pp. 641-648, 2003.
Kulkarni et al., "Neurosteroids: A New Clas of Neuromodulators," *Drugs of Today*, vol. 31, No. 6, pp. 433-455, 1995.
Rupprecht, "Neuroactive steroids: mechanisms of action and neuropsychopharmacological properties," *Psychoneuroendocrinology*, vol. 28, pp. 139-168, 2003.
Smith, "Withdrawal properties of a neuroactive steroid: implications for $GABA_A$ receptor gene regulation in the brain and anxiety behavior," *Steroids*, vol. 67, pp. 519-528, 2002.
Rupprecht et al., "Neuroactive Steroids in Neuropsychopharmacology," *International Review of Pharmacology*, vol. 48, pp. 461-477, 2001.
Rupprecht et al., "Neuroactive steroids: molecular mechanisms of action and implications for neuropsychopharmacology," *Brain Research Reviews*, vol. 37, pp. 59-67, 2001.
Lukasiuk et al., "$GABA_A$—Mediated Toxicity of Hippocampal Neurons in Vitro," *Journal of Neurochemistry*, vol. 74, No. 6, pp. 2445-2454, 2000.
Van Den Pol et al., "Glutamate Hyperexcitability and Seizure-Like Activity Throughout the Brain and Spinal Cord Upon Relief from Chronic Glutamate Receptor Blockade in Culture," *Neuroscience*, vol. 74, No. 3, pp. 653-674, 1996.
Extended European Search Report issued on Feb. 22, 2012 in application No. EP 11177154.9.
He et al., "Allopregnanolone, a progesterone metabolite, enhances behavioral recovery and decreases neuronal loss after traumatic brain surgery;" Restorative Neurology and Neuroscience, vol. 22, pp. 19-31, 2004.
Reder et al., "A reduction in serum glucocorticoids provokes experimental allergic encephalomyelitis: Implications for treatment of inflammatory brain disease," Neurology, vol. 44, pp. 2289-2294, Dec. 1994.
Adams et al., "Steroid withdrawal in liver transplant recipients," Progress in Transplantation, vol. 11, No. 3, pp. 217-223, Sep. 2001.
Office Action issued on May 16, 2012 by the Examiner in U.S. Appl. No. 13/045,180 (US 2011/0224181).
Wilson et al., "Free Radicals, Antioxidants, and Neurologic Injury: Possible Relationship to Cerebral Protection by Anesthetics," Journal of Neurosurgical Anesthesiology, vol. 14, No. 1, pp. 66-79, 2002.

\* cited by examiner

A.

B.

A.

B.

+4.2   +3.2   +2.2

METHODS FOR THE TREATMENT OF A CENTRAL NERVOUS SYSTEM INJURY VIA A TAPERED ADMINISTRATION PROTOCOL

This application is a continuation of U.S. patent application Ser. No. 11/909,276, filed May 13, 2009, which is a U.S. national stage of International application number PCT/US2006/10984, filed Mar. 24, 2006, which claims priority to U.S. Provisional patent application No. 60/664,728, filed Mar. 24, 2005, and U.S. Provisional patent application No. 60/729,663, filed Oct. 24, 2005.

FEDERALLY SPONSORED RESEARCH OR DEVELOPMENT

This invention was made with United States Government support under grant numbers R01 N5038664-04 and R01 N5040825-03 awarded by the National Institute of Neurological Disorders and Stroke (NINDS) of the National Institutes of Health. The United States Government has certain rights in the invention.

FIELD OF THE INVENTION

The invention relates to methods for treating a traumatic or ischemic injury to the central nervous system.

BACKGROUND OF THE INVENTION

There is growing experimental evidence that progesterone, its metabolites and other gonadal steroids such as estrogen and possibly testosterone, are effective neuroprotective agents; although the specific, physiological mechanisms by which these hormones act in the central nervous system to enhance repair are not completely understood. In addition to being a gonadal steroid, progesterone also belongs to a family of autocrine/paracrine hormones called neurosteroids. Neurosteroids are steroids that accumulate in the brain independently of endocrine sources and which can be synthesized from sterol precursors in glial cells. These neurosteroids can potentiate GABA transmission, modulate the effects of glutamate, enhance the production of myelin, reduce the expression of inflammatory cytokines and prevent release of free radicals from activated microglia.

In vivo data has demonstrated progesterone's neuroprotective effects in injured nervous systems. For example, following a contusion injury, progesterone reduces the severity of post injury cerebral edema. The attenuation of edema by progesterone is accompanied by the sparing of neurons from secondary neuronal death and improvements in cognitive outcome (Roof et al. (1994) *Experimental Neurology* 129:64-69). Furthermore, following ischemic injury in rats, progesterone has been shown to reduce cell damage and neurological deficit (Jiang et al. (1996) *Brain Research* 735:101-107). Progesterone's protective effects may be mediated thorough its interaction with GABA and/or glutamate receptors as well as its effects on inflammatory cytokines and aquaporin expression which are mediated by the intranuclear progesterone receptor.

Various metabolites of progesterone have also been suggested to have neuroprotective properties. For instance, the progesterone metabolites allopregnanolone or epipregnanolone are positive modulators of the GABA receptor, increasing the effects of GABA in a manner that is independent of the benzodiazepines (Baulieu, E. E. (1992) *Adv. Biochem. Psychopharmacol.* 47:1-16; Robel et al. (1995) *Crit. Rev. Neurobiol.* 9:383-94; Lambert et al. (1995) *Trends Pharmacol. Sci.* 16:295-303; Baulieu, E. E. (1997) *Recent Prog. Horm. Res.* 52:1-32; Reddy et al. (1996) *Psychopharmacology* 128:280-92). In addition, these neurosteroids act as antagonists at the sigma receptor: a receptor that can activate the NMDA channel complex (Maurice et al. (1998) *Neuroscience* 83:413-28; Maurice et al. (1996) *J. Neurosci. Res.* 46:734-43; Reddy et al. (1998) *Neuroreport* 9:3069-73). These neurosteroids have also been shown to reduce the stimulation of cholinergic neurons and the subsequent release of acetylcholine by excitability. Numerous studies have shown that the cholinergic neurons of the basal forebrain are sensitive to traumatic brain injury and that excessive release of acetylcholine can be more excitotoxic than glutamate (Lyeth et al. (1992) *J. Neurotrauma* 9(2):S463-74; Hayes et al. (1992) *J. Neurotrauma* 9(1):S173-87).

Following a traumatic injury to the central nervous system, a cascade of physiological events leads to neuronal loss including, for example, an inflammatory immune response and excitotoxicity resulting from the initial impact disrupting the glutamate, acetylcholine, cholinergic, $GABA_A$, and NMDA receptor systems. In addition, the traumatic CNS injury is frequently followed by brain and/or spinal cord edema that enhances the cascade of injury and leads to further secondary cell death and increased patient mortality.

Other kinds of CNS injury can set into motion different physiological events that lead to neuronal loss. For example, ischemic injury occurs when blood flow to the CNS is interrupted. During ischemia, consumed cellular ATP usually cannot be adequately replenished in the absence of a supply of oxygen. Other physiological events associated with ischemic CNS injury include release or overexpression of proteins such as neuron-specific enolase (NSE), myelin basic protein, glial fibrillary acidic protein (GFAP), the S-100 protein, and the gamma isoform of protein kinase C (PKCg), stimulation of membrane phospholipid degradation and subsequent free-fatty-acid accumulation, cellular acidosis, glutamate release and excitotoxicity, calcium ion influx, and free radical generation.

Significant ischemia in the CNS occurs with stroke, leading to rapid cell death in the core regions of the stroke where blood flow is reduced to about 20% of normal levels. However, there is a larger area of potential injury, called the ischemic penumbra, where blood flow is reduced to a lesser extent. Cells in this region are endangered, but may not be irreversibly damaged.

Because of limitations in current therapies for CNS injuries as described above, improved methods for treating traumatic and ischemic CNS injury are needed.

SUMMARY OF THE INVENTION

Methods for the treatment or the prevention of neuronal damage in the CNS are provided. In particular, the present invention provides a method of administration of a therapeutically effective amount of a progestin or progestin metabolite following a traumatic or ischemic injury to the CNS such that, prior to termination of the progestin or progestin metabolite administration is tapered to avoid withdrawal. The drug taper employed can involve a linear taper, an exponential taper, progressively dividing administered doses by 50%, or can be determined based on the treating physician's assessment of the patient's response to therapy. The tapered administration methods of the present invention may be used in combination with any therapeutic protocol or regimen for the administration of a therapeutically effective amount of a progestin or progestin metabolite to treat a traumatic or ischemic CNS injury.

BRIEF DESCRIPTION OF THE DRAWINGS

FIG. 1 shows a dosage response curve for behavioral recovery following a traumatic brain injury.

FIG. 3A shows that at one day post-withdrawal, TWL animals showed decreased latency compared to VL and AWL animals (#, $p<0.05$). AWS rats demonstrated elevated sensory deficiencies compared to the TWS and VS groups (*, $p<0.05$). FIG. 3B shows that at one week post-withdrawal, sham animals demonstrated equivalent latency, while tapered treatment maintained decreased latency compared to acute and vehicle treatment (#, $p<0.05$).

FIG. 4A shows that one day after withdrawal, center time was increased for TWS animals compared to all other shams (#, $p<0.05$), while TWL center time was increased compared to other lesion groups (**, $p<0.05$). AWL animals increased center time compared to vehicle animals (##, $p<0.05$), and AWS animals significantly decreased center time compared to VS animals (*, $p<0.05$). FIG. 4B showed that TWL center time one week after withdrawal is increased over AWL (**, $p<0.05$), which is increased over VL (##, $p<0.05$). No difference was seen between sham groups.

FIG. 8A shows representative thionin-stained sections at mm anterior to bregma for lesion animals. FIG. 8B shows percent lesion volume at 3 weeks post-injury is greatest in vehicle-treated animals, followed by those with acute withdrawal (*, $p<0.05$) and tapered withdrawal (#, $p<0.05$).

FIG. 9 shows immunofluorescent staining for GFAP in brain slices from the following groups: (A) VL; (B) AWL; (C) TWL; (D) VS; (E) AWS; and (F) TWS. Images are shown at 40×, with 10 µm represented. FIG. 10 shows quantification of luminosity for GFAP immunofluorescent staining of reactive astrocytes indicates the greatest response in VL (*, $p<0.05$) animals, followed by AWL (**, $p<0.05$) and TWL animals. AWS animals had significantly elevated levels of reactive astrocytes compared to other sham groups m (#, $p<0.05$).

DETAILED DESCRIPTION OF THE INVENTION

Figure 1A:
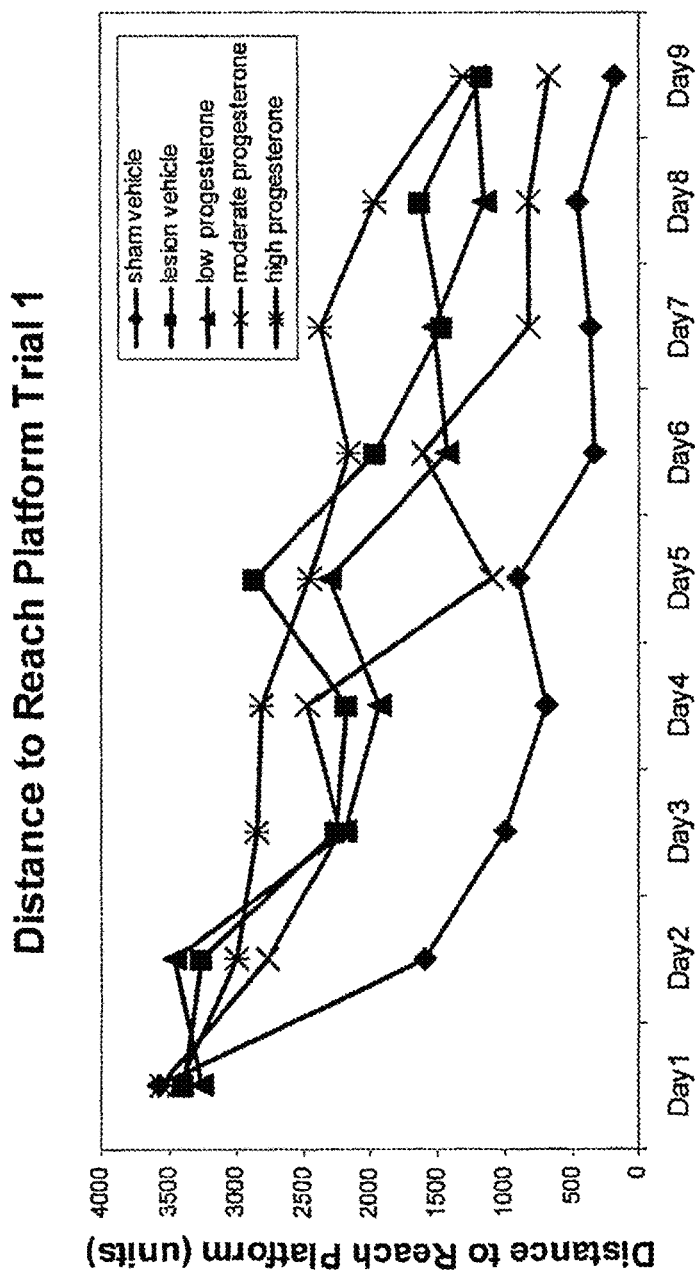
FIGS. 1A and 1B demonstrate that following treatment with low (8 mg/kg), moderate (16 mg/kg), and high (32 mg/kg) doses of progesterone in a cyclodextrin-containing carrier, both low and moderate doses of progesterone produced consistent improvement in Morris water maze performance.
Figure 1B:
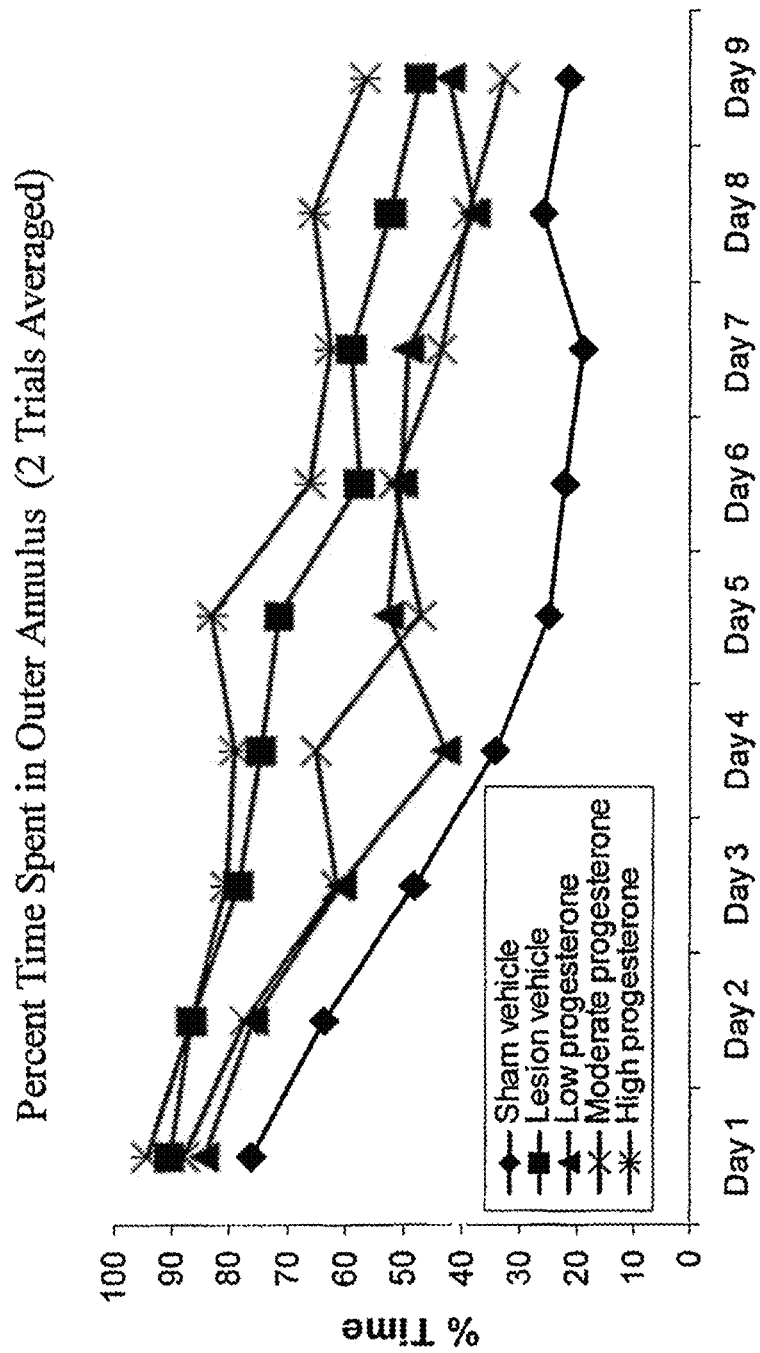

The present invention provides methods and compositions for the treatment or prevention of neurodegeneration following a traumatic or ischemic injury to the central nervous system. In particular, the methods of the invention provide for the administration of a therapeutically effective amount of a progestin or progestin metabolite following a traumatic or ischemic injury to the CNS such that, prior to termination of administration of the progestin or progestin metabolite the administration is tapered to avoid withdrawal. As described in further detail elsewhere herein, the present invention demonstrates that the tapered administration allows for a more beneficial CNS repair than when an abrupt termination of the progestin or progestin metabolite occurs.

By "treatment" is intended any improvement in the subject having the traumatic or ischemic injury including both improved morphological (i.e., enhanced tissue viability) and/or behavioral recovery. The improvement can be characterized as an increase in either the rate and/or the extent of behavioral and anatomical recovery following the traumatic or ischemic CNS injury. Accordingly, a "positive therapeutic response" induces both a complete response and a partial response. Various methods to determine if a complete or partial therapeutic response has occurred are disclosed elsewhere herein.

Neurodegeneration is the progressive loss of neurons in the central nervous system. As used herein, "neuroprotection" is the arrest and/or reverse progression of neurodegeneration following a traumatic or ischemic central nervous system injury. Hence, the methods of the invention also find use in reducing and/or preventing the physiological events leading to neurodegeneration. Specifically, the present invention provides methods for reducing or eliminating neuronal cell death, edema, ischemia, and enhancing tissue viability following a traumatic or ischemic injury to the central nervous system.

The sex hormones are steroids that may be classified into functional groups according to chemical structure and physiological activity and include estrogenic hormones, progestational hormones, and androgenic hormones. Of particular interest in the methods of the present invention are progestational hormones, referred to herein as "progestins" or "progestogens", and their derivatives and bioactive metabolites. Members of this broad family include steroid hormones disclosed in *Remington's Pharmaceutical Sciences*, Gennaro et al., Mack Publishing Co. ($18^{th}$ ed. 1990), 990-993. As with all other classes of steroids, sterioisomerism is of fundamental importance with the sex hormones. Hence, a variety of progestins (i.e., progesterone) and their derivatives are encompassed by the present invention, including both synthetic and natural products. In one aspect of the invention, the progestin or progestin metabolite is progesterone.

The term "progesterone" as used herein refers to a member of the progestin family and comprises a 21 carbon steroid hormone. Progesterone is also known as D4-pregnene-3,20-dione; δ4-pregnene-3,20-dione; or pregn-4-ene-3,20-dione and it its structure is provided below as formula (I). The progesterone used in the methods of the invention can be naturally occurring or synthetic.

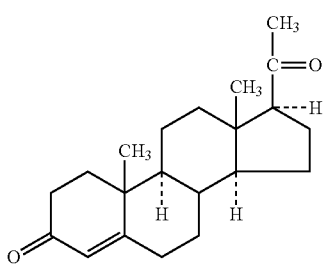

Formula I

Further encompassed by the methods of the invention are synthetic progestins. As used herein a "synthetic progestin" is a molecule whose structure is related to that of progesterone, is synthetically derived, and retains the biologically activity of progesterone (i.e., treats a traumatic CNS injury). Representative synthetic progestin include, but are not limited to, modifications that produce 17a-OH esters (i.e., 17α-hydroxyprogesterone caproate), as well as, modifications that introduce 6 α-methyl, 6-Me, 6-ene, and 6-chloro substituents onto progesterone (i.e., medroxyprogesterone acetate, megestrol acetate, and chlomadinone acetate). Table 1 provides further, non-limiting examples, of synthetic progestins.

TABLE 1

Classification of Synthetic Progestins

| Classification by structure | Usual classification by generation* | | |
|---|---|---|---|
| | First | Second | Third |
| Estranes | Ethynodiol diacetate (with ethinyl estradiol: Demulen) Norethindrone (Micronor) Norethindrone acetate (Aygestin) | — | — |
| Gonanes | Norgestrel (Ovrette) | Levonorgestrel (Norplant; with ethinyl estradiol: Alesse, Nordette) | Desogestrel (with ethinyl estradiol: Desogen) Gestodene† Norgestimate (with ethinyl estradiol: Ortho-Cyclen, Ortho Tri-Cyclen) |
| Pregnanes | Medroxyprogesterone acetate (Provera) | — | — |

*The traditional classification is based on time since market introduction and not on structural and physiologic differences or efficacy.

As used herein, by "bioactive metabolite" or "derivative" of progestin is intended any naturally or synthetically produced progestin that prevents or retards neurodegeneration. Such progestin derivatives include, for example, derivatives of progesterone, such as 5-dehydroprogesterone, 6-dehydroretroprogesterone (dydrogesterone), allopregnanolone (allopregnan-3α, or 3β-ol-20-one), ethynodiol diacetate, hydroxyprogesterone caproate (pregn-4-ene-3,20-dione, 17-(1-oxohexy)oxy); levonorgestrel, norethindrone, norethindrone acetate (19-norpregn-4-en-20-yn-3-one, 17-(acetyloxy)-, (17α)-); norethynodrel, norgestrel, pregnenolone, and megestrol acetate. Useful progestins also can include allopregnone-3α or 3β, 20α or 20β-diol (See Merck Index 258-261); allopregnane-3β,21-diol-11,20-dione; allopregnane-3β,17α-diol-20-one; 3,20-allopregnanedione, allopregnane,3β,11β, 17α,20β,21-pentol; allopregnane-3β,17α,20β21-tetrol; allopregnane-3α or 3β,11β,17α,21-tetrol-20-one, allopregnane-3β,17α or 20β-triol; allopregnane-3β,17α,21-triol-11,20-dione; allopregnane-3β,11β,21-triol-20-one; allopregnane-3β,17α,21-triol-20-one; allopregnane-3α or 3β-ol-20-one; pregnanediol; 3,20-pregnanedione; pregnan-3α-ol-20-one; 4-pregnene-20,21-diol-3,11-dione; 4-pregnene-11β,17α, 20β,21-tetrol-3-one; 4-pregnene-17α,20β,21-triol-3,11-dione; 4-pregnene-17α,20β,21-triol-3-one, and pregnenolone methyl ether. Further progestin derivatives include esters with non-toxic organic acids such as acetic acid, benzoic acid, maleic acid, malic acid, caproic acid, citric acid and the like. Inorganic salts include, for example, hydrochloride, sulfate, nitrate, bicarbonate and carbonate salts. Additionally, compounds that may find use in the present invention include the progestin derivatives that are disclosed in U.S. Pat. No. 5,232,917, herein incorporated by reference.

The progestin or progestin metabolite may be administered per se or in the form of a pharmaceutically acceptable salt. When used in medicine, the salts of the progestin or progestin metabolite should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of a progestin or progestin metabolite with an organic or inorganic acid, using standard methods detailed in the literature. Examples of pharmaceutically acceptable salts are organic acids salts formed from a physiologically acceptable anion, such as, tosglate, methenesulfurate, acetate, citrate, malonate, tartarate, succinate, benzoate, etc. Inorganic acid salts can be formed from, for example, hydrochloride, sulfate, nitrate, bicarbonate and carbonate salts. Also, pharmaceutically acceptable salts can be prepared as alkaline metal or alkaline earth salts, such as sodium, potassium, or calcium salts of the carboxylic acid group.

A traumatic injury to the CNS is characterized by a physical impact to the central nervous system. For example, a traumatic brain injury results when the brain is subjected to a physical force that results in progressive neuronal cell damage and/or cell death. A traumatic brain injury may result from a blow to the head and manifests as either an open or closed injury. For example, blast injuries are caused by the complex pressure wave generated by an explosion, and can include closed injuries such as concussion without external signs of head trauma. Other physical forces that may act on the brain include increased intracranial pressure due to, for example, subarachnoid or intracranial hemorrhage, tumor growth, ventriculomegaly, or cerebral edema. Severe brain damage can occur from lacerations, skull fractures, and conversely, even in the absence of external signs of head injury. The physical forces resulting in a traumatic brain injury cause their effects by inducing three types of injury: skull fracture, parenchymal injury, and vascular injury.

Parenchymal injuries include concussion, direct parenchymal injury and diffuse axonal injury. Concussions are characterized as a clinical syndrome of alteration of consciousness secondary to head injury typically resulting from a change in the momentum of the head (movement of the head arrested against a ridged surface). The pathogenesis of sudden disruption of nervous activity is unknown, but the biochemical and physiological abnormalities that occur include, for example, depolarization due to excitatory amino acid-mediated ionic fluxes across cell membranes, depletion of mitochondrial adenosine triphosphate, and alteration in vascular permeability. Postconcussive syndrome may show evidence of direct parenchymal injury, but in some cases there is no evidence of damage.

Contusion and lacerations are conditions in which direct parenchymal injury of the brain has occurred, either through transmission of kinetic energy to the brain and bruising analogous to what is seen in soft tissue (contusion) or by penetration of an object and tearing of tissue (laceration). A blow to the surface of the brain leads to rapid tissue displacement, disruption of vascular channels, and subsequent hemorrhage, tissue injury and edema. Morphological evidence of injury in the neuronal cell body includes pyknosis of nucleus, eosinophilia of the cytoplasm, and disintegration of the cell. Furthermore, axonal swelling can develop in the vicinity of damage neurons and also at great distances away from the site of impact. This phenomenon can be characterized as "diffuse neuronal injury" and is caused by stretching and shearing of the axon. The inflammatory response to the injured tissue follows its usual course with neutrophiles preceding the appearance of macrophages.

An ischemic injury to the CNS is characterized by an insufficiency or interruption in the blood supply to any locus of the brain such as, but not limited to, a locus of the cerebrum, cerebellum or brain stem. The spinal cord, which is also a part of the CNS, is equally susceptible to ischemia resulting from diminished blood flow. An ischemic episode may be caused by a constriction or obstruction of a blood vessel, as occurs in the case of a thrombus or embolus. Alternatively, the ischemic episode may result from any form of compromised cardiac function, including cardiac arrest. Where the deficiency is sufficiently severe and prolonged, it can lead to disruption of physiologic function, subsequent death of neurons, and necrosis (infarction) of the affected areas. The extent and type of neurologic abnormality resulting from the injury depend on the location and size of the infarct or the focus of ischemia. Where the ischemia is associated with a stroke, it can be either global or focal in extent.

Global ischemia, as used herein in reference to the CNS, refers to a condition that results from a general diminution of blood flow to the entire brain, forebrain, or spinal cord, which causes the delayed death of neurons, particularly those in metabolically active loci, throughout these tissues.

Focal ischemia, as used herein in reference to the CNS, refers to a condition that results from the blockage of a single artery that supplies blood to the brain or spinal cord, resulting in the death of all cellular elements (pan-necrosis) in the territory supplied by that artery.

As described above, the present invention provides a method for treating or preventing neuronal damage caused by a traumatic or ischemic injury to the CNS through the administration of a therapeutically effective amount of a progestin or progestin metabolite such that, prior to termination of administration of the progestin or progestin metabolite the administration is tapered to avoid withdrawal. As described in more detail in the Experimental Section below, the present invention relates to the finding that, when stopping progesterone therapy, tapered administration of progesterone to avoid withdrawal results in greater efficacy of progesterone therapy compared to abrupt termination of administration.

By "tapered administration" or "tapered administration dosing regimen" is meant successive reduced doses and eventual elimination of the progestin or progestin metabolite, either over a fixed period of time or a time determined empirically by a physician's assessment based on regular monitoring of a therapeutic response of a patient to a traumatic or ischemic CNS injury. The period of the tapered progestin or progestin metabolite administration can be about 12, 24, 36, 48 hours or longer. Alternatively, the period of the tapered progestin or progestin metabolite administration can range from about 1 to 12 hours, about 12 to about 48 hours, or about 24 to about 36 hours. In one aspect of the invention, tapered administration of a progestin or progestin metabolite involves tapered administration of progesterone.

The drug taper employed could involve progressively dividing administered doses by 50%. For example, such a taper from 500 mg would go 500, 250, 125, 62.5, etc. The drug taper employed could be a "linear" taper. For example, a "10%" linear taper from 500 mg would go 500, 450, 400, 350, 300, 250, 200, 150, 100, 50, etc. Alternatively, an exponential taper could be employed which, if the program outlined above is used as an example, the exponential taper would be, e.g., 500, 450, 405, 365, 329, 296, 266, 239, etc. Accordingly, about a 5%, 10%, 20%, 30%, or 40% linear or exponential taper could be employed in the methods of the invention. In addition, a linear or exponential taper of about 1% to 5%, about 6% to 10%, about 11% to 15%, about 16% to 20%, about 21% to 25%, about 26% to 30%, about 31% to 35%, about 36% to 40% could be employed. Alternatively, the taper schedule can be determined based on the treating physician's assessment of the patient's response to therapy.

The tapered administration methods of the present invention are used in combination with administration of progestin or progestin metabolite therapies for subjects having traumatic or ischemic CNS injury. As defined herein, the subject can be any mammal, preferably a human or an animal, including domestic, agricultural, or exotic animals. In specific embodiments, the human is an adult (over 18 years of age), while in other embodiments, the human is a child (under 18 years of age). The child can be a neonate, infant, toddler, pre-pubescent or post-pubescent and range in age from about birth, 1 month to about 2 year, about 1 year to about 5 years, about 4 years to about 9 years, about 8 years to about 14, or about 13 to about 18 years of age. In addition, the human can be about 55 to 60, 60 to 65, 65 to 70, 70 to 75, 75 to 80, 80 to 85, 85 to 90, 90 to 95 or older.

Prior to the tapered administration of the present invention, the progestin or progestin metabolite is administered at a therapeutically effective level to a subject in need thereof for the treatment of a CNS injury. By "therapeutically effective amount" is meant the concentration of a progestin or progestin metabolite that is sufficient to elicit a therapeutic effect. Thus, the concentration of a progestin or progestin metabolite in an administered dose unit in accordance with the present invention is effective in the treatment or prevention of neuronal damage that follows a traumatic or ischemic injury to the CNS and hence, elicits a neuroprotective effect. The therapeutically effective amount will depend on many factors including, for example, the specific activity of the progestin or progestin metabolite, the severity, pattern, and type of injury (e.g., traumatic or ischemic), the resulting neuronal damage, the responsiveness of the patient, the weight of the patient along with other intraperson variability, the method of administration, and the progestin or progestin metabolite formulation used. Various methods for administering a therapeutically effective amount of the progestin or progestin metabolite treat CNS injury, including determination of efficacy, dosage, and route of administration, are known in the art (see, e.g., U.S. Patent Application No. 60/664,728 filed Mar. 24, 2005, and U.S. patent application Ser. No. 09/973,375, filed Oct. 9, 2001, both of which are herein incorporated by reference). Any therapeutic protocol or regimen for the administration of a therapeutically effective amount of progestin or progestin metabolite to treat a traumatic or ischemic CNS injury may be used in combination with the tapered administration method of the present invention.

In one embodiment of the invention, the tapered administration methods of the present invention are used in combination with administration of progestin or progestin metabolite at least once a day, including administration once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

For instance, a dosage unit can be administered from about 0 hours to about 1 hr, about 1 hr to about 24 hours, about 1 to about 72 hours, about 1 to about 120 hours, or about 24 hours to at least about 120 hours post injury. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. For instance, additional dosage units can be administered to protect the patient from the secondary wave of edema that may occur over the first several days post-injury.

In another embodiment of the invention, the tapered administration methods of the present invention are used in combination with a constant progesterone or synthetic progestin dosing regimen. By "constant progesterone or synthetic progestin dosing regimen" is intended the patient undergoing therapy with the progesterone or synthetic progestin is administered a constant total hourly dose of the progesterone or synthetic progestin over the course of treatment. This hourly dose of the progesterone or synthetic progestin is partitioned into a series of equivalent doses that are administered according to an appropriate dosing schedule depending on the method of administration. The duration of the constant progesterone or synthetic progestin dosing regimen is about 12, 24, 36, 60, 72, 84, or 120 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours.

In other embodiments of the invention, the tapered administration methods of the present invention are used in combination with a "two-level progesterone or synthetic progestin dosing regimen." By "two-level progesterone or synthetic progestin dosing regimen" is intended the patient undergoing the therapy with the progesterone or synthetic progestin is administered the progesterone or synthetic progestin during two time periods of progesterone or synthetic progestin dosing. The two-time periods can have a combined duration of about 12 hours to about 7 days, including, 1, 2, 3, 4, or 5 days or about 15, 15, 30, 35, 40, 45, 50, 55, 60, 65, 70, 75, 80, 85, 90, 95, 100, 105, 110, 115, 120, 125, 130, 135, 140, or 144 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours. In one embodiment, the two-level progesterone or synthetic progestin dosing regimen has a combined duration of about 1 day to about 5 days; in other embodiments, the two-level progesterone or synthetic progestin dosing regimen has a combined duration of about 1 day to about 3 days.

In one embodiment, the total hourly dose of the progesterone or synthetic progestin that is to be administered during the first and second time periods of the two-level progesterone or synthetic progestin dosing regimen is chosen such that a higher total hourly dose of the progesterone or synthetic progestin is given during the first time period and a lower hourly dose of the progesterone or synthetic progestin is given during the second time period. The duration of the individual first and second time periods of the two-level progesterone or synthetic progestin dosing regimen can vary, depending upon the health of the individual and history of the traumatic or ischemic injury. Generally, the patient is administered higher total hourly dose of progesterone or synthetic progestin for at least 1, 2, 3, 4, 5, 6, 12 or 24 hours out of the 1 day to 5 day two-level progesterone or synthetic progestin dosing regimen. The length of the second time period can be adjusted accordingly, and range for example, from about 12 hrs, 24 hrs, 36 hrs, 48 hrs, 60 hrs, 72 hrs, 84 hrs, 96 hrs, 108 hrs, 120 his or about 12 to about 36 hrs, about 24 to about 36 hrs, about 24 to about 48 hrs, about 36 hrs to about 60 hours, about 48 hrs to about 72 hrs, about 60 hrs to about 84 hours, about 72 hrs to about 96 his, or about 108 hrs to about 120 hrs. Thus, for example, where the two-level progesterone or synthetic progestin dosing regimen has a combined duration of 3 days, the higher total doses of the progesterone or synthetic progestin could be administered for the first hour, and the lower total hourly dose of the progesterone or synthetic progestin could be administered for hours 2 to 72.

In still further embodiments, the total hourly dose of progestrone that is to be administered during the first and second time periods of the two-level progesterone or synthetic progestin dosing regimen is chosen such that a lower total hourly dose of the progesterone or synthetic progestin is given during the first time period and a higher hourly dose of the progesterone or synthetic progestin is given during the second time period.

Area under the curve (AUC) refers to the area under the curve that tracks the serum concentration (nmol/L) of the progesterone or synthetic progestin over a given time following the IV administration of the reference progesterone or synthetic progestin standard. By "reference progesterone or synthetic progestin standard" is intended the formulation of the progesterone or synthetic progestin that serves as the basis for determination of the total hourly progesterone or synthetic progestin dose to be administered to a human patient with a traumatic or ischemic central nervous system injury in accordance with the desired constant or two-level progesterone or synthetic dosing regimen to achieve the desired positive effect, i.e., a positive therapeutic response that is improved with respect to that observed without administration of the progesterone or synthetic progestin. Accordingly, the total hourly dose of progesterone or synthetic progestin to be administered during the constant or two-level progesterone or synthetic progestin dosing regimen can therefore allow for a final serum level of the progesterone or synthetic progestin of about of about 100 ng/ml to about 1000 ng/ml, about 1100 ng/ml to about 1450 ng/ml, 100 ng/ml to about 250 ng/ml, about 200 ng/ml to about 350 ng/ml, about 300 ng/ml to about 450 ng/ml, about 400 ng/ml to about 550 ng/ml, about 500 ng/ml to about 650 ng/ml, about 600 ng/ml to about 750 ng/ml, about 700 ng/ml to about 850 ng/ml, about 800 ng/ml to about 950 ng/ml, about 900 ng/ml to about 1050 ng/ml, about 1000 ng/ml to about 1150 ng/ml, about 1100 ng/ml to about 1250 ng/ml, about 1200 ng/ml to about 1350 ng/ml, about 1300 ng/ml to about 1500 ng/m. In specific embodiments, the serum level of the progesterone or synthetic progestin comprises about 100 ng/ml, 250 ng/ml, 500 ng/ml, 750 ng/ml, 900 ng/ml, 1200 ng/ml, 1400 ng/ml, 1600 ng/ml.

The tapered administration methods of the present invention also contemplate embodiments where a patient undergoing a constant progesterone or synthetic progestin therapy or a two-level progesterone or synthetic dosing regimen is given a time period off from progesterone or synthetic dosing. For example, when a progesterone or synthetic progestin dosing regimen is performed, the time period off from the progesterone or synthetic progestin can occur between the conclusion of the first time period of the two-level progesterone or synthetic progestin dosing regimen and the initiation of the second time period of the two-level progesterone or synthetic progestin dosing regimen. For example, one could contemplate the first time period being administered in a pre-hospital setting, for instance at the site of the trauma. The second time period could then begin upon arrival at a hospital. In these embodiments, the two-level progesterone or synthetic progestin dosing regimen is interrupted such that progesterone or synthetic progestin dosing is withheld for a period of about 15 minutes, 30 minutes, 1 hr, 2 hrs, 3 hrs, 4 hrs, 5 hrs, 6 hrs or more.

Where a patient undergoing therapy in accordance with the previously mentioned dosing regimens exhibits a partial response, or a relapse following completion of therapy, subsequent courses of progesterone or synthetic progestin therapy may be needed to achieve a partial or complete therapeutic response. Thus, subsequent to a period of time off from treatment, which may have comprised a constant progesterone or synthetic progestin dosing regimen or a two-level progesterone or synthetic progestin dosing regimen, a patient may receive one or more additional treatment periods comprising either constant or two-level progesterone or synthetic progestin dosing regimens. Such a period of time off between treatment periods is referred to herein as a time period of discontinuance. It is recognized that the length of the time period of discontinuance is dependent upon the degree of patient response (i.e., complete versus partial) achieved with any prior treatment periods of the progesterone or synthetic progestin therapy. It is further recognized that prior to a period of time off or discontinuance, administration of the progesterone or synthetic progestin therapy may be tapered.

For use with the tapered administration methods of the present invention, multiple treatment sessions are referred to herein as maintenance cycles, where each maintenance cycle comprises a completed dosing regimen. By "completed two-level dosing regimen" is intended the patient has been administered both the first period and the second period of progesterone or synthetic progestin dosing. The necessity for multiple maintenance cycles can be assessed by monitoring the Physiological and behavioral improvement of the patient. The duration between maintenance cycles can be about 1 hr, 15 hrs, 1 day, 2 day, 3 day, 4 day, 5 day, 6 day or other such time periods falling within the range of about 1 day to about 14 days.

For use in the tapered administration methods of the present invention, progestin or progestin metabolite may further comprise an inorganic or organic, solid or liquid, pharmaceutically acceptable carrier. The carrier may also contain preservatives, wetting agents, emulsifiers, solubilizing agents, stabilizing agents, buffers, solvents and salts. Compositions may be sterilized and exist as solids, particulants or powders, solutions, suspensions or emulsions. In addition to the aforementioned ingredients, the compositions of the invention may further include one or more accessory ingredient(s) selected from the group consisting of diluents, buffers, flavoring agents, binders, disintegrants, surface active agents, thickeners, lubricants, preservatives (including antioxidants) and the like.

The progestin or progestin metabolite can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences* (16th ed., Osol, A. (ed.), Mack, Easton Pa. (1980)). In order to form a pharmaceutically acceptable composition suitable for effective administration, such compositions will contain an effective amount of the progestin or progestin metabolite, either alone, or with a suitable amount of carrier vehicle.

The pharmaceutically acceptable carrier will vary depending on the method of drug administration and may be, for example, either a solid, liquid, or time release. Representative solid carriers are lactose, terra alba, sucorse, talc, geletin, agar, pectin, acacia, magnesium stearate, stearic acid, microcrystalin cellulose, polymer hydrogels, and the like. Typical liquid carriers include syrup, peanut oil, olive oil, cyclodextrin, and the like emulsions. Those skilled in the art are familiar with appropriate carriers for each of the commonly utilized methods of administration. Furthermore, it is recognized that the total amount of progestin or progestin metabolite administered as a therapeutic effective dose will depend on both the pharmaceutical composition being administered (i.e., the carrier being used) and the mode of administration.

Compositions for use in the methods of the present invention include those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier or both, and then, if necessary, shaping the product into desired formulations.

Compositions for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parental administration conveniently comprise a sterile aqueous preparation of the active compound, which can be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Further, compositions for use in the methods of the present invention include liposomal formulations. The technology for forming liposomal suspensions is well known in the art. When the progestin or progestin metabolite salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer that forms the structure of the liposome. In either instance, the liposomes that are produced may be reduced in size, as through the use of standard sonication and homogenization techniques. The liposomal formulations containing the progestin or progestin metabolite or salts thereof, may be lyophilized to produce a lyophilizate which may be reconstituted with a pharmaceutically acceptable carrier, such as water, to regenerate a liposomal suspension.

Pharmaceutical formulations for use in the methods of the present invention also include those which are suitable for administration as an aerosol, by inhalation. These formulations comprise a solution or suspension of the desired progestin or progestin metabolite or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts.

Further pharmaceutical formulations for use in the methods of the present invention include controlled release preparations. Such controlled release preparations may be achieved by the use of polymers to complex or absorb the progestin or progestin metabolite. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, polylactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980).

For use in the methods of the present invention, compositions comprising a therapeutically effective concentration of progestin or progestin metabolite may be administered using any acceptable method known in the art. Thus, for example, the pharmaceutical composition comprising progestin or progestin metabolite can be administered methods that include intravenous (IV), intramuscular (IM), subcutaneous (SC), intraperitoneal, transdermal, buccal, vaginal, or intracerebroventricular administration. When administered intravenously, the pharmaceutical composition comprising progesterone or synthetic progestin can be administered by infusion over a period of about 1 to about 120 hours. In some embodiments, infusion of progesterone or synthetic progestin occurs over a period of about 24 to about 72 hours, over a period of about 48 to about 96 hours, or over a period of about 24 to about 120 hours.

An embodiment of the present invention provides for the administration of a progesterone or synthetic progestin or analogue thereof via IV administration in a dose of about 0.1 ng to about 100 g per kg of body weight, about 10 ng to about 50 g per kg of body weight, from about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of progesterone or synthetic progestin administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In another embodiment of the present invention provides for the administration of a progestin or progestin metabolite or analogue thereof via parenteral administration in a dose of about 0.1 ng to about 100 g per kg of body weight, about 10 ng to about 50 g per kg of body weight, from about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of progestin or progestin metabolite administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater. In one aspect of the invention, the progestin or progestin metabolite for parenteral administration is progesterone or allopregnanolone.

In further embodiments of the present invention, the tapered administration methods of the invention are used in combination with the use of a progestin or progestin metabolite and at least one additional neuroprotective agent to enhance neuroprotection following a traumatic or ischemic CNS injury. Such agents include, for example, any combination of progestin or progestin metabolite. Other neuroprotective agents of interest include, for example, compounds that reduce glutamate excitotoxicity and enhance neuronal regeneration. Such agents may be selected from, but not limited to, the group comprising growth factors. By "growth factor" is meant an extracellular polypeptide-signaling molecule that stimulates a cell to grow or proliferate. Preferred growth factors are those to which a broad range of cell types respond. Examples of neurotrophic growth factors include, but are no limited to, fibroblast growth factor family members such as basic fibroblast growth factor (bFGF) (Abraham et al. (1986) *Science* 233:545-48), acidic fibroblast growth factor (aFGF) (Jaye et al. (1986) *Science* 233:541-45), the hst/Kfgf gene product, FGF-3 (Dickson et al. (1987) *Nature* 326-833), FGF-4 (Zhan et al. (1988) *Mol. Cell. Biol.* 8:3487-3495), FGF-6 (deLapeyriere et al. (1990) *Oncogene* 5:823-831), keratinocyte growth factor (KGF) (Finch et al. (1989) *Science* 245:752-755), and androgen-induced growth factor (AIGF) (Tanaka et al. (1992) *Proc. Natl. Acad. Sci. USA* 89:8928-8923).

Additional neuroprotective agents include, ciliary neurotrophic factor (CNTF), nerve growth factor (NGF) (Seiler, M. (1984) *Brain Research* 300:33-39; Hagg T. et al. (1988) *Exp Neurol* 101:303-312; Kromer L. F. (1987) *Science* 235: 214-216; and Hagg T. et al. (1990) *J. Neurosci* 10(9):3087-3092), brain derived neurotrophic factor (BDNF) (Kiprianova, I. et al. (1999) *J. Neurosci. Res.* 56:21-27), Neurotrophin 3 (NT3), Neurotrophin 4 (NT4), transforming growth factor-β1 (TGF-β1) (Henrick-Noack, P. et al. (1996) *Stroke* 27:1609-14), bone morphogenic protein (BMP-2) (Hattori, A. et al. (1999) *J. Neurochem.* 72:2264-71), glial-cell line derived neurotrophic factor (GDNF) (Miyazaki, H. et al. (1999) *Neuroscience* 89:643-7), activity-dependant neurotrophic factor (ADNF) (Zamostiano, R. et al. (1999) *Neurosci Letter* 264:9-12), cytokine leukemia inhibiting factor (LIF) (Blesch, A. et al. (1999) *J. Neurosci.* 19:3356-66), oncostatin M, interleukin, and the insulin-like growth factors 1 and 2.

Other forms of neuroprotective therapeutic agents include, for example, Clomethiazole (Zendra) (Marshal, J. W. et al. (1999) *Exp. Neurol.* 156:121-9); kynurenic acid (KYNA) (Salvati, P. et al. (1999) *Prog Neruopsychopharmacol Biol Psychiatry* 23:741-52), Semax (Miasoedova, N. F. et al. (1999) *Zh Nevrol Psikhiatr Imss Korsakova* 99:15-19), FK506 (tacrolimus) (Gold, B. G. et al. (1999) *J. Pharmacol. Exp. Ther.* 289:1202-10), L-threo-1-phenyl-2-decanoylamino-3-morpholino-1-propanol (Inokuchi, J. et al. (1998) *Act Biochim Pol* 45:479-92), andrenocorticotropin-(4-9) analogue (ORG 2766) and dizolcipine (MK-801) (Herz, R. C. et al. (1998) *Eur J. Pharmacol* 346:159-65), cerebral interleukin-6) (Loddick, S. A. et al. (1998) *J. Cereb Blood Flow Metab* 18:176-9), selegiline (Semkova, I. et al., (1996) *Eur J. Pharmacol* 315:19-30), MK-801 (Barth, A. et al., (1996) *Neuro Report* 7:1461-4; glutamate antagonist such as, NPS1506, GV1505260, MK801 (Baumgartner, W. A. et al. (1999) *Ann Thorac Surg* 67:1871-3), GV150526 (Dyker, A. G. et al. (1999) *Stroke* 30:986-92); AMPA antagonist such as NBQX (Baumgartner, W. A. (1999) et al. *Ann Thorac Surg* 67:1871-3, PD152247 (PNQX) (Schielke, G. P. et al. (1999) *Stroke* 30:1472-7), SPD 502 (Nielsen, E. O. et al. (1999) *J. Pharmacol Exp Ther* 289:1492-501), LY303070 and LY300164 (May, P. C. et al. (1999) *Neuroscience Lett* 262: 219-221).

Where the tapered administration methods of the invention are used in combination with the use of a progestin or progestin metabolite and at least one additional neuroprotective agent to enhance neuroprotection following a traumatic or ischemic CNS injury, it is recognized that even less of the progestin or progestin metabolite may be required to be therapeutically effective.

The methods of the present invention find use in treating a traumatic or ischemic injury of the central nervous system. Methods to quantify the extent of central nervous system damage (i.e., neurodegeneration) and to determine if neuronal damage was treated or prevented following the administration of a progestin or progestin metabolite are well known in the art. Such neuroprotective effects can be assayed at various levels, including, for example, by promoting behavioral and morphological (i.e., enhancing tissue viability) recovery after traumatic or ischemic brain injury. A variety of anatomical, immunocytochemical and immunological assays to determine the effect of the progestin or progestin metabolite on necrosis, apoptosis, and neuronal glial repair are known in the art. As such, the neuroprotection resulting from the methods of the present invention will result in at least about a 10% to 20%, 20% to 30%, 30% to 40%, 40% to 60%, 60% to 80% or greater increase in neuronal survival and/or behavioral recovery as compared to the control groups.

Histological and molecular marker assays for an increase in neuronal survival are known. For example, Growth Associated Protein 43 (GAP-43) can be used as a marker for new axonal growth following a CNS insult. See, for example, Stroemer et al. (1995) *Stroke* 26:2135-2144, Vaudano et al. (1995) *J. of Neurosci.* 15:3594-3611. Other histological markers can include a decrease in astrogliosis and microgliosis. Alternatively, a delay in cellular death can be assayed using TUNEL labeling in injured tissue. Further anatomical measures that can be used to determine an increase in neuroprotection include counting specific neuronal cell types to determine if the progestin or progestin metabolite is preferentially preserving a particular cell type (e.g., cholinergic cells) or neurons in general.

In addition, behavioral assays can be used to determine the rate and extent of behavior recovery in response to the treatment. Improved patient motor skills, spatial learning performance, cognitive function, sensory perception, speech and/or a decrease in the propensity to seizure may also be used to measure the neuroprotective effect. Such functional/behavioral tests used to assess sensorimotor and reflex function are described in, for example, Bederson et al. (1986) *Stroke* 17:472-476, DeRyck et al. (1992) *Brain Res.* 573:44-60, Markgraf et al. (1992) *Brain Res.* 575:238-246, Alexis et al. (1995) *Stroke* 26:2336-2346; all of which are herein incorporated by reference. Enhancement of neuronal survival may also be measured using the Scandinavian Stroke Scale (SSS) or the Barthl Index. Behavioral recovery can be further assessed using the recommendations of the Subcommittee of the NIH/NINDS Head Injury Centers in Humans (Hannay et al. (1996) *J. Head Trauma Rehabil.* 11:41-50), herein incorporated by reference. Behavioral recovery can be further assessed using the methods described in, for example, Beaumont et al. (1999) *Neurol. Res.* 21:742-754; Becker et al. (1980) *Brain Res.* 200:07-320; Buresov et al. (1983) *Techniques and Basic Experiments for the Study of Brain and Behavior*; Kline et al. (1994) *Pharmacol. Biochem. Behav.* 48:773-779; Lindner et al. (1998) *J. Neurotrauma* 15:199-216; Morris (1984) *J. Neurosci. Methods* 11:47-60; Schallert et al. (1983) *Pharmacol. Biochem. Behav.* 18:753-759.

It is recognized that a traumatic injury to the CNS results in multiple physiological events that impact the extent and rate of neurodegeneration, and thus the final clinical outcome of the injury. The treatment of a traumatic injury to the CNS, as defined by the present invention, encompasses any reduction and/or prevention in one or more of the various physiological events that follow the initial impact. Hence, the methods of the invention find use in the reduction and/or prevention of physiological events leading to neurodegeneration following a traumatic injury to the central nervous system.

For instance, cerebral edema frequently develops following a traumatic injury to the CNS and is a leading cause of death and disability. Cortical contusions, for example, produce massive increases in brain tissue water content which, in turn, can cause increased intracranial pressure leading to reduced cerebral blood flow and additional neuronal loss. Hence, the methods of the invention find use in reducing and/or eliminating cerebral edema and/or reducing the duration of the edemic event following a traumatic injury to the CNS. Assays to determine a reduction in edema are known in the art and include, but are not limited to, a decrease in tissue water content following the administration of the progestin or progestin metabolite (Betz et al. (1990) Stroke 21:1199-204, which is herein incorporated by reference). Furthermore, an overall improvement in behavioral recovery can also be used as a measure for a decrease in edema. A decrease in edema in the effected tissue by at least about 15% to 30%, about 30% to 45%, about 45% to 60%, about 60% to 80%, or about 80% to 95% or greater will be therapeutically beneficial, as will any reduction in the duration of the edemic event Vasogenic edema following a traumatic brain injury has been associated with damage to the vasculature and disruption of the blood-brain barrier (BBB) (Duvdevani et al. (1995) J. Neurotrauma 12:65-75, herein incorporated by reference). Progesterone has been shown to reduce the permeability of the BBB to macromolecules, but not ions, such as sodium in vitro (Betz et al. (1990) Stroke 21:1199-204; Beta et al. (1990) Acta. Neurochir. Suppl. 51:256-8; both of which are herein incorporated by reference). Hence, the methods of the invention find use in reducing or eliminating vasogenic edema following a traumatic brain injury. Assays to determine a decrease in vasogenic edema are known in the art and include, for instance, a reduction in Evans' blue extravasation after cortical contusion (Roof et al. (1994) Society for Neuroscience 20:91, herein incorporated by reference).

Further physiological effects of a traumatic brain injury include an immune response. See, for example, Soares et al. (1995) J. Neurosci. 15:8223-33; Holmin et al. (1995) Acta Neurochir. 132:110-9; Arvin et al. (1996) Neurosci. Biobehav. Rev. 20:445-52. Following a cortical impact, severe inflammatory reactions and gliosis at the impact site and at brain areas distal to the primary site of injury occurs. The inflammatory response is characterized by the expression of adhesion molecules on the vascular surfaces, resulting in the adherence of immune cells and subsequent extravasation into the brain parenchyma. By releasing cytokines, the invading macrophages and neutrophils stimulate reactive astrocytosis. Release of different chemokines by other cell types induces these immune cells to become phagocytic, with the simultaneous release of free radicals and pro-inflammatory compounds, e.g., cytokines, prostaglandins, and excitotoxins (Arvin et al. (1996) Neurosci. Biobehav. Ref 20:445-52; Raivich et al. (1996) Kelo J. Med. 45:239-47; Mattson et al. (1997) Brain Res. Rev. 23:47-61; all of which are herein incorporated by reference).

The methods of the invention provide a means to reduce or eliminate the inflammatory immune reactions that follow a traumatic CNS injury. Furthermore, by reducing the inflammatory response following an injury, the progestin or progestin metabolite of the present invention can substantially reduce brain swelling and intracranial pressure and reduce the amount of neurotoxic substances (e.g., free radicals and excitotoxins) that are released. Therefore, by reducing the immune/inflammatory response following a traumatic injury to the CNS, neuronal survival and/or behavioral recovery will be enhanced.

Assays that can be used to determine if the progestin or progestin metabolite of the invention is imparting an anti-inflammatory and a nonspecific suppressive effect on the immune system following a traumatic CNS injury include, for example, a reduction in cytokine induced microglial proliferation in vitro (Hoffman et al. (1994) J. Neurotrauma 11:417-31; Garcia-Estrada et al. (1993) Brain Res. 628:271-8; both of which are herein incorporated by reference); a reduction in the generation of cytotoxic free radicals by activated macrophages (Chao et al. (1994) Am. J. Reprod. Immunol. 32:43-52; Robert et al. (1997) Nitric Oxide 1:453-62; Kelly et al. (1997) Biochem. Biophys. Res. Commmun. 239: 557-61; Canter et al. (1992) J. Neurosci. Res. 33:218-30; all of which are herein incorporated by reference); a reduction in the expression of inducible nitric oxide synthetase and the amount of nitric oxide release by macrophages (Robert et al. (1997) Nitric Oxide 1:453-62; Miller et al. (1996) J. Leukoc. Biol. 59:442-50; both of which are herein incorporated by reference); the release of a "progesterone-induced blocking factor" that inhibits natural killer cell activity (Cheek et al. (1997) Am. J. Reprod. Immunol. 37:17-20; Szekeres-Bartho et al. (1997) Cell Immunol. 177:194-9; Szekeres-Bartho et al. (1996) Am. J. Reprod. Immunol. 35:348-51; all of which are herein incorporated by reference); a decrease in the number of GFAP-positive astrocytes after brain injury which is suggestive of less secondary damage (Garcia-Estrada et al. (1993) Brain Res. 628:271-8; Garcie-Estrada et al. (1999) Int. J. Dev. Neurosci. 17:145-51; Cheek et al. (1997) Am. J. Reprod. Immunol. 37:17-20; Szekeres-Bartho et al. (1997) Cell Immunol. 177:194-9; Szekeres-Bartho et al. (1996) Am. J. Reprod. Immunol. 35:348-51; all of which are herein incorporated by reference); a reduction in the number of inflammatory immune cells (OX42-positive cells); a reduction in the loss of ChAT-positive and COX-positive neurons; a reduction in the number of TUNEL-positive and MnSOD-positive neurons; and an increase in the intensity of succinate dehydrogenase and cytochrome oxidase activity.

Furthermore, a reduction in the inflammatory immune reactions following a traumatic brain injury can be assayed by measuring cytokine level following the injury in the sham controls versus the progestin or progestin metabolite treated subjects. Cytokines are mediators of inflammation and are released in high concentrations after brain injury. The level of pro-inflammatory cytokines (e.g., interleukin 1-beta, tumor necrosis factor, and interleukin 6) and the level of anti-inflammatory cytokines (e.g., interleukin 10 and transforming growth factor-beta) can be measured. For instance, "real-time" polymerase chain reactions (PCR) can be used to measure the strength of the mRNA signal and ELISA can be used to determine protein levels. In addition, histological analysis for different inflammatory cell types (e.g., reactive astrocytes, macrophages and microglia) can be used to measure a reduction in the inflammatory response.

Another physiological consequence of a traumatic CNS injury is an increase in lipid peroxidation. The methods of the invention find use in reducing free radical damage and thus decreasing or eliminating lipid peroxidation. This effect may occur through an enhancement of endogenous free radical scavenging systems. Assays to measure a reduction in lipid peroxidation in both brain homogenate and in mitochondria are known in the art and include, for example, the thiobarbituric acid method (Roof et al. (1997) Mol. Chem. Neuropathol. 31:1-11; Subramanian et al. (1993) Neurosci. Lett. 155:151-4; Goodman et al. (1996) J. Neurochem. 66:1836-44; Vedder et al. (1999) J. Neurochem. 72:2531-8; all of which are herein incorporated by reference) and various in vitro free radical generating systems Furthermore, alterations in the levels of critical free radical scavenger enzymes, such as mitochondrial glutathione can be assayed. See, for example, Subramanian et al. (1993) Neurosci. Lett. 155:151-4; and Vedder et al (1999) J. Neurochem. 72:2531-8; both of which are herein incorporated by reference.

Furthermore, cultured, cytokine-stimulated macrophages generate nitrite, superoxide, and hydrogen peroxide. Since macrophages are known to be very active between 48 hours and seven days after a traumatic brain injury, a reduction in these reactive cells would reduce secondary damage to neurons. See, for example, Fulop et al. (1992) $22^{nd}$ Annual Meeting of the Society for Neuroscience 18:178; Soares et al. (1995) *J. Neurosci.* 15:8223-33; Holmin et al. (1995) *Acta Neurochir.* 132:110-9; all of which are herein incorporated by reference.

It is recognized that an ischemic injury to the CNS results in its own set of physiological events that impact the extent and rate of neurodegeneration, and thus the final clinical outcome of the injury. The treatment of an ischemic injury to the CNS, as defined by the present invention, encompasses any reduction and/or prevention in one or more of the various physiological events that follow the initial interruption in blood supply. Hence, the methods of the invention find use in the reduction and/or prevention of physiological events leading to or associated with neurodegeneration following an ischemic injury to the central nervous system.

As described elsewhere herein, ischemic CNS injury is associated with certain physiological events leading to neurodegeneration, including, for example, release or overexpression of proteins such as NSE, myelin basic protein, GFAP, the S-100 protein, and PKCg, stimulation of membrane phospholipid degradation and subsequent free-fatty-acid accumulation, energy failure due to ATP depletion, cellular acidosis, glutamate release and excitotoxicity, calcium ion influx, and free radical generation. Assays to determine a reduction and/or prevention of physiological events leading to or associated with neurodegeneration following an ischemic CNS injury may be directed toward measuring any of these physiological events. For example, assays for measuring levels of NSE, myelin basic protein, GFAP, the S-100 protein, and PKCg are well known in the art (see, e.g., Missler et al. (1997) *Stroke*, 28:1956-1960; Shashoua et al. (1984) *J. Neurochem.*, 42:1536-1541; and U.S. Pat. No. 6,268,223; all of which are incorporated herein by reference). Assays for measuring a decrease in serum levels of fatty acids may be determined by methods well known in the art such as taught in U.S. Pat. Nos. 4,071,413; 5,512,429; 5,449,607; and 4,369,250, all of which are incorporated herein by reference.

Other assays for determining a reduction and/or prevention of physiological events leading to or associated with neurodegeneration following an ischemic CNS injury may be directed toward clinical assessments of, for example, a decrease in infarct area, improved body weight, and improved neurological outcome. Such clinical assays are well known to those of skill in the art.

Having now generally described this invention, the same will be better understood by reference to certain specific examples which are included herein for purposes of illustration only, and are not intended to be limiting of the invention, unless specified.

EXPERIMENTAL

Example 1

Effects of Progesterone on Necrotic Damage and Behavioral Abnormalities Caused by TBI Methods:

Male Sprague-Dawley rats (300 g) were housed individually in wire cages and kept on a reverse light-dark cycle (0800-2000 h). Animals were assigned to one of four groups: (1) lesion (n=7); (2) lesion+3 days progesterone (LP3; n=7); (3) lesion+5 days progesterone (LP5; n=7); and (4) Sham (n=8). All procedures involving animals conformed to guidelines set forth in the Guide for the Care and Use of Laboratory Animals (U.S. Department of Health and Human Services, Pub no. 85-23, 1985) and were approved by the Emory University Institutional Animal Care and Use Committee.

Bilateral contusions of the medial prefrontal cortex were created by a pneumatic impactor device as previously described [40]. Briefly, rats were given anesthetized with ketamine/xylazine (90 mg/kg; 10 mg/kg) and placed in a stereotaxic apparatus. A craniectomy (diameter 6 mm) was made over the midline of the prefrontal cortex with its center 1.5 mm AP to bregma. After removal of the bone, the tip of the impactor (diameter 5 mm) was moved to +3.0 mm AP; 1.0 mm ML (from bregma), and checked for adequate clearance. Trauma was produced by pneumatically activating the piston to impact −2.0 mm DV (from dura) at a velocity of 3 m/s with a brain contact time of 0.5 seconds.

Progesterone was dissolved in peanut oil (Sigma; 4 mg/kg) and injections were given at 1 and 6 hours post-injury and then once per day for either 3 or 5 consecutive days. Control animals received injections of vehicle at similar time-points. Animals were coded with regard to surgery and treatment to prevent experimenter bias during behavioral testing and histological examination.

Twenty-one days after surgery, animals were perfused with 100 ml 0.1 M phosphate-buffered saline (PBS; pH 7.4) followed by 400 ml 4% paraformaldehyde in 0.1 M phosphate buffer (PB; pH 7.4). Following cryoprotection in 30% sucrose, coronal 40-μm-thick sections were cut on a freezing microtome, immediately mounted on gel-coated slides and stained for Nissl with thionine to determine placement and extent of the injury.

Mean area measurements of lesion size were quantified from sections at 15 rostral-caudal levels spaced 300 μm apart. The perimeter of the necrotic cavity (including injured penumbra) was traced on digitized images using the Jandel Scientific SigmaScan software calibrated to calculate the area in $mm^2$ for each level traced. Perimeters of the striatum and the lateral ventricles were also traced and mean areas were quantified from 7 rostral-caudal levels (300 μm apart).

Cell counts were done on an Olympus BH-2 microscope equipped with an eyepiece micrometer grid (sample area=40 $um^2$ at ×400 magnification). Bilateral cell counts of Nissl-stained neurons were made on 3 separate sections in each of the following areas: (1) STR (+1.8 to +1.2 mm AP), (2) GP (−0.3 to −1.2 mm AP), (3) DMN (−2.3 to −2.9 mm AP), and (4) VMN (−2.3 to −2.9 mm AP). Only cells with neuronal nuclei and intact membranes were counted as neurons.

Experienced individuals who were blind to treatment conditions of the study conducted all histological and behavioral analyses. All data were tested for normality and homoschedasticity before being analyzed by parametric analysis of variance (ANOVA). MWM results were analyzed using separate mixed-factorial (4 groups×5 days) analysis of variance (ANOVA) on each of the two 5-day testing periods (acquisition and retention respectively). Results of the BSN task were analyzed using the mixed-factorial ANOVA (4 groups×2 post-injury trials). Histological comparisons on mean densitometry recordings, area measurements, and cell counts were made using a one-way ANOVA. All between-group comparisons were made using multiple Tukey post-hoc tests ($p<0.05$) when the overall ANOVA was significant ($p<05$) between groups. Pearson r coefficients were calculated to determine whether significant correlations could be detected between histological (e.g., lesion size and cellular density) and behavioral parameters (e.g., acquisition and retention of the MWM task and measures of sensory neglect).

Beginning one week after surgery, spatial learning ability was assessed in the Morris water maze (MWM) task described previously. Each animal was tested for a total of 10 days in two 5-day trial blocks (acquisition and retention respectively). Animals were placed in the pool (nose facing the pool-wall) at one of four randomly determined starting positions (e.g.: N, S, E, W). Each rat was allowed to swim freely in the pool until it found the hidden platform or until 90 seconds had elapsed. If an animal did not find the platform in 90 seconds, he was manually guided to it. Once on the platform, animals were allowed to rest for 10 seconds and then removed from the pool and placed near a heat lamp for warmth. Each rat was given two trials per day with a 20-second intertrial interval (ITI). The dependent measures for this task were latency to find the hidden platform and swim strategy (e.g., percent of time spent in the inner vs. outer annuli). Swim speed measures were recorded daily in order to delineate motor dysfunction from learning impairment.

Measures of attentional abilities, using a bilateral sensory neglect (BSN) task, were recorded one day prior to surgery (baseline) and on postsurgical days 6 and 20. Pairs of circular adhesive papers (2 cm dia) were attached to the distal-radial areas of each forepaw and the rats' latencies to remove the stimuli were recorded. Each rat was given four trials (2-min ITI) per testing period with a maximum trial length of 2 minutes. If the rats did not remove the adhesive disks within the standard time, a total latency of 2 minutes was recorded for that trial.

Results:

Histology.

In most animals, necrotic tissue was primarily restricted to the medial prefrontal and cingulate cortex. However, in some cases, more severe tissue damage extended into the corpus callosum and the most dorsal aspects of the medial septum and striatum (Data not shown). A significant main effect on necrotic cavity formation was observed between the three injured groups, ($F_{2,19}=3.57$, $P<0.05$). Tukey post hoc analysis revealed a dose-dependent reduction in necrotic cavity formation. Data not shown. Notably, all animals that were given progesterone tended to have smaller lesions compared to injured animals that were given vehicle injections. However, only 5 days of progesterone resulted in significant reductions in overall necrotic cavity formation ($P<0.05$). We also observed enlargement of the lateral ventricles in all injured groups as compared to control animals ($F_{3,25}=5.28$, $P<0.01$) but progesterone did not have any effect on this measure. Data not shown. No between-group differences were shown on measures of mean striatal area.

One-way ANOVA revealed a main effect of mean cellular density between groups on counts taken in the STR ($F_{3,25}=15.58$, $P<0.01$), GP ($F_{3,25}=4.47$, $P<0.01$), DMN ($F_{3,25}=5.37$, $P<0.01$), and VMN ($F_{3,25}=8.68$, $P<0.01$). Results of Tukey post hoc tests showed that both LP3 and LP5 treatments resulted in a significant reduction of injury-induced neuronal loss in all brain regions examined. However, 5 days of progesterone was more effective than 3 days at attenuating neuronal loss in the VMN, the area most distal to injured penumbra. Data not shown.

Behavioral Testing.

In the MWM task, all of the injured groups displayed deficits in spatial learning performance as compared to control animals during the initial 5-day acquisition phase ($F_{3,25}=19.45$, $P<0.01$). However, Tukey post hoc tests detected improved spatial learning performance in LP5, but not LP3, animals during the second 5-day trial block ($F_{3,25}=6.76$, $P<0.01$). Data not shown.

ANOVA revealed a significant main effect on swim patterns during acquisition ($F_{3,25}=28.23$, $P<0.01$) and retention ($F_{3,25}=12.25$, $P<0.01$) of the MWM task. Data not shown. All the injured animals displayed sustained thigmotaxic (wall-hugging) swim patterns during the first 5-day MWM trial block. But a reduction of thigmotaxic behavior was observed in the LP5-treated animals in the last 2 days of the second phase of MWM testing ($P>0.05$ compared to controls) corresponding with the reduction in latency to find the platform observed in this group. There were no between-group differences on swim speed measurements on any day of testing.

There were no between-group differences on baseline measures of sensory neglect recorded one day prior to surgery. A significant main effect between groups ($F_{3,25}=6.17$, $P<0.01$) was observed in results of the BSN task following controlled cortical contusion to the medial prefrontal cortex. Tukey post hoc analysis showed that only the LP3-treated animals were impaired on this task compared to control animals at both 6 and 20 days post injury (Data not shown).

We also detected significant correlations between histological measures and performance in the MWM task. Specifically, there was a positive correlation between necrotic cavity formation and improved MWM performance during the second 5-day trial block, suggesting that smaller lesions resulted in improved retention of this task ($r_{21}=+0.44$, $P<0.05$). Similarly, we observed a negative correlation between cellular density and spatial learning performance during the second phase of MWM testing ($r_{21}=-0.50$, $P<0.05$) which indicates that progesterone-mediated neuronal sparing allowed for greater functional recovery (data not shown). Finally, we did not observe any significant correlations between either lesion size or cellular density and measures of sensory neglect.

Summary:

The reduction of the injury-induced necrotic cavity formation provides evidence that a post-injury neurosteriod intervention might reduce lesion volume following TBI in this animal model. In the present study, we observed a dose-dependent reduction in necrotic cavity formation in progesterone treated animals. Specifically, while the necrotic cavities in the brains of animals treated with only 3 days of progesterone (LP3) tended to be smaller than in the brains of injured animals, only the 5-day treatment regimen (LP5) resulted in significantly smaller lesions. Our study now provides the first evidence that progesterone may also attenuate TBI-induced tissue loss.

In our study, progesterone also protected against secondary cell loss in brain regions both proximal (e.g., STR) and distal (e.g., GP, DMN, and VMN) to the zone of injury. Interestingly, in the present study, both 3 and 5 days of progesterone treatment reduced neuronal loss in the STR, GP, and DMN, but only LP5-treatments produced significant reductions in cell loss of the VMN compared to untreated controls.

And finally, in the present study, all injured groups were impaired on the acquisition phase of MWM testing. The LP5 animals showed clear improvement, albeit not to control levels, in spatial performance during the retention phase of this task. Significant correlations were found between neuropathological parameters (e.g., necrotic cavity formation and neuronal sparing) and MWM performance demonstrating that progesterone-mediated reductions in lesion size cell death resulted in concomitant reductions in latency to find the platform.

Example 2

Dosage Response Curves for Behavioral Recovery Following TBI Upon Administration of Progesterone in a Cylcodextrin Vehicle Methods:

Surgery to induce a traumatic brain injury was performed as outlined in Example 1. Behavior testing using the Morris Water Maize was performed as outlined in Example 1 and the methods for the tactical adhesive removal were performed.

Results:

FIGS. 1A and 1D demonstrate that low and moderate doses of progesterone (8 mg/kg & 16 mg/kg in a cyclodextrin-containing vehicle) produced consistent improvement in Morris water maze performance, whereas the high dose of progesterone (32 mg/kg in a cyclodextrin-containing vehicle) did not show any beneficial effect.

Figure 2:
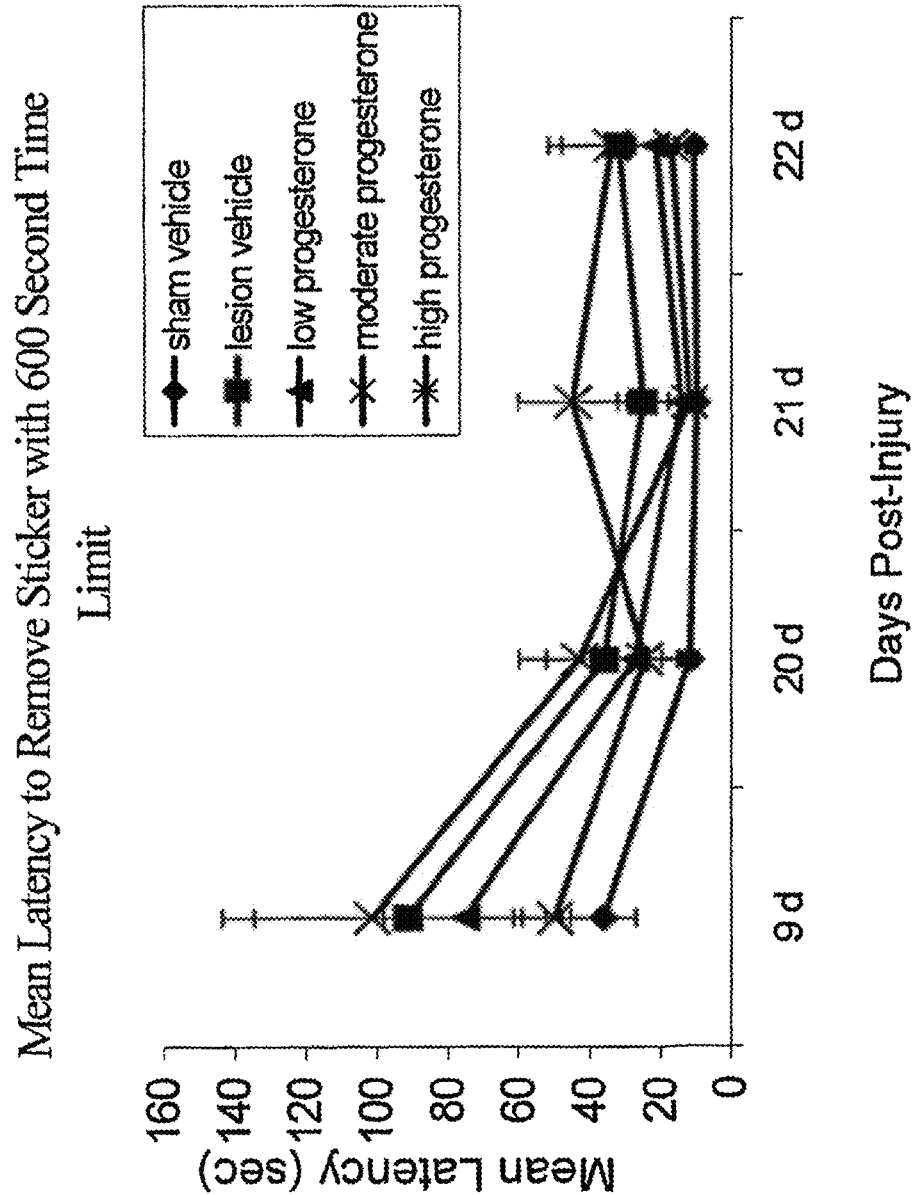
FIG. 2 shows the results from the "sticker removal task" following treatment with low (8 mg/kg), moderate (16 mg/kg), and high (32 mg/kg) dosages of progesterone in a cyclodextrin-containing carrier.

The sticker removal task is a test for sensory neglect which is a primary deficit for frontal injury. In this task all doses initially produce behavioral recovery, however, the group receiving the high dose of progesterone degraded to lesion control levels and the moderate dose, which was initially at lesion control levels improved to sham levels by day 21 post-injury. See FIG. 2.

Example 3

Tapered Progesterone Withdrawal Enhances Recovery after Traumatic Brain Injury

Methods:

Male Sprague-Dawley rats received either medial frontal cortex injury or sham surgery. Injections were given 1 and 6 hours post-injury, and every 24 hours for 7 days. Treatment groups (n=8) encompassed injured (I) and sham (S) acute withdrawal (AW), tapered withdrawal (TW) and vehicle (V) treatments. TW injections were progressively halved over the final two treatments. Behavioral testing was conducted post-surgery, mid- and post-withdrawal. Activity boxes were used to investigate vertical movements and exploration: Sensory neglect and anxiety behaviors were also analyzed. Brain harvesting was performed at 8 days or 3 weeks post-injury. Perfused tissue sections were analyzed for lesion volume and immunohistochemical response. Fresh brain tissue was flash frozen in chilled 2-methyl butane, and then homogenized for Western blot analysis.

Results:

Acute withdrawal and injury (AWI) interacted to increase anxiety, locomotor and sensory deficits compared to tapered progesterone withdrawal (TWI). Additionally, acute withdrawal-shams (AWS) had increased motor impairments compared to all other shams, and increased anxiety compared to tapered progesterone rats. The neuroprotective factors BDNF and HSP70 increased for TWI over AWI over VI at 3 weeks post-injury. This beneficial effect of tapered hormone treatment correlated with lesion reconstruction and GFAP staining; TWI animals had the smallest lesion volume and fewest reactive astrocytes, followed by AWI while VI had the largest lesion volume and most reactive astrocytes. Apoptosis and inflammation were decreased with TW, as demonstrated by p53, active Caspase 3, TNFα and NFκB.

Conclusion:

Acute PW has a compelling effect on both behavior and tissue recovery after traumatic brain injury. At the peak of withdrawal, animals undergoing progesterone withdrawal syndrome exhibit increased anxiety, sensory deficits, and locomotor deficits; all of these are further exacerbated by injury. One week later, increased behavioral impairments are still evident in AWI animals. Western blotting revealed decreased expression of apoptotic and inflammatory proteins with tapered withdrawal, although all progesterone treatments led to better outcomes compared to vehicle-only controls. At 3 weeks post-injury, the compound effect of lesions and acute progesterone withdrawal continued to cause behavioral deficits over those animals with a gradual decrease in progesterone treatment. These findings can be taken to suggest that in clinical testing, tapered withdrawal of progesterone will be more beneficial to CNS repair than an abrupt termination of the treatment at the end of the dosage regime.

Example 4

Tapered Progesterone Withdrawal Promotes Long-Term Recovery After Traumatic Brain Injury Having demonstrated that after TBI, AW causes an increase in anxiety behaviors and cerebro-cellular inflammation compared to TW (see Example 3), this study investigated the behavioral and cellular effects of AW two weeks after termination of treatments to determine the longer-term influence of withdrawal after injury.

As described above, progesterone treatment following traumatic brain injury and stroke reduces the effects of secondary injury and necrosis (Asbury et al. (1998) *Behav. Brain Res.*, 97:99-106; Attella et al. (1987) *Behav. Neural. Biol.*, 48:352-367; Chen et al. (1999) *J. Neural. Sci.*, 171:24-30; Galani et al., (2001) *Restor. Neural. Neurosci.*, 18:161-166; Gibson et al. (2005) *Exp. Neurol*, 193:522-530; Gibson and Murphy (2004) *J. Cereb. Blood Flow Metab.*, 24:805-813; Grossman et al. (2004) *Brain Res.*, 1008:29-39; Kumon et al. (2000) *J. Neurosurg.*, 92:848-852; Roof et al. (1994) *Exp. Neurol.*, 129:64-69; Roof et al. (1994) "Progesterone Reduces BBB Damage Following Bilateral, Medial Frontal Contusion," in Twenty-first Annual Meeting of the Society for Neuroscience, Miami Beach, Fla., p. 191; Roof et al. (1997) *Mol. Chem. Neuropathol.*, 31:1-11; Shear et al. (2002) *Exp. Neurol.*, 178:59-67; Vink and Van Den Heuvel (2004) *Expert Opin. Investig. Drugs*, 13:1263-1274). AW, however, results in an increase in apoptosis, inflammation and anxiety behaviors during the acute recovery phase after TBI compared to TW (Cutler et al. (2005) *Exp. Neurol.*, 195(2):423-429). All animals given progesterone, regardless of their treatment regime, showed improvement over vehicle-treated animals, but those animals with TW had better recovery as evidenced by less inflammation, apoptosis and functional anxiety. AW causes anxiety, depression, and increased seizure susceptibility due to a sudden decrease in GABA-A interactions with allopregnanolone, a progesterone metabolite (Foldvary-Schaefer et al. (2004) *Cleve. Clin. J. Med.*, 71:S11-18; Gulinello et al. (2003) *Eur. J. Neurosci.*, 17:641-648; Kulkami and Reddy (1995) *Drugs Today*, 31:433-455; Rupprecht (2003) *Psychoneuroendocrinology*, 28:139-168; Smith (2002) *Steroids*, 67:519-528). The resulting increase in NMDA activation leads to an excitatory neural environment (Lukasiuk and Pitkanen (2000) *J. Neurochem.*, 74:2445-2454; Van Den Pol et al. (1996) *Neuroscience*, 74:653-674). Under the added stress of trauma, this effect is amplified to an increased excitotoxicity. With gradual withdrawal, this excitotoxicity, secondary injury and inflammation are not exacerbated.

In this study, the effects of AW on functional recovery measured three weeks post-TBI were studied. To follow up on the finding that Caspase-3, a keystone protein in apoptosis (Budihardjo et al. (1999) *Annu. Rev. Cell Dev. Biol.* 15:269-290), is increased at the time of withdrawal, up- or downregulation of a long-term marker of apoptosis, p53, was measured (Harris and Levine (2005) *Oncogene* 24:2899-2908). The p53 protein alters the permeability of mitochondrial membranes, allowing for the release of cytochrome C, which induces the activation of apoptotic proteases, including caspase-3 (Mattson (2003) *Neuromolecular Med.* 3:65-94). Also, to determine if neuroprotection is enhanced by TW, HSP70 and BDNF were measured, as well as necrotic lesion cavity size and reactive gliosis. Both BDNF and HSP70 act to promote synaptic plasticity and the release of trophic factors (Binder and Scharfman (2004) *Growth Factors* 22:123-131; Feinstein et al. (1996) *J. Biol. Chem.* 271:17724-17732), while a reduction in necrotic lesion size indicates protection and sparing of neuronal cells. Furthermore, past studies have shown that progesterone plays a part in the reduction of reactive astrocytes associated with cerebral edema and inflammation (Djebaili et al. (2005) *J. Neurotrauma* 22:106-118); this benefit may also be enhanced with tapered withdrawal.

Given the widespread effects of acute withdrawal previously noted at the peak of withdrawal, it was predicted that these effects would manifest themselves in long-term behavioral testing after the initial cascade of secondary injury has subsided. Accordingly, locomotor activity and somatosensory neglect were assayed for subject groups undergoing TW versus AW, from one to three weeks after injury.

Materials and Methods:

Subjects.

60 male Sprague-Dawley rats weighing 290-310 g at the time of injury were used in this experiment. Food and water were provided ad libitum before and after surgery. Animals were handled and weighed daily from their arrival, seven days pre-surgery, to brain extraction three weeks post-surgery. Animals were handled in squads of 12, with n=10 per experimental condition. All animal procedures were approved by the Emory University Animal Care and Use Committee, Protocol #131-2002.

Surgery.

Isofluorane anesthesia was induced for four minutes and 45 seconds at 5% and maintained at 2.5%. Normal body temperature was maintained with a surgical heating pad placed beneath the sterile dressings. The scalp incision area was shaved and sterilized with iodine and isopropanol. A midline incision was made along the scalp and the fascia cleared to expose the surface of the skull. Medial, lateral, and dorsal stereotaxic coordinates were determined at bregma, and a 5-7 mm diameter bilateral craniotomy was performed mid-sagitally, 3 mm anterior to bregma. Medial frontal cortex (MFC) injury was created with a pneumatic cortical contusion device (5 mm diameter) at a pressure of 1.7 psi, over 50 ms with a velocity of 2.25 m/s and to a depth of 2.5 mm. Sutures were used to close the incision after bleeding ceased. Animals were placed in individual heated, clean recovery cages until they awakened, and were returned to clean individual home cages with accessible moistened food pellets. Sham animals were anesthetized, and an incision was made at the top of the head. The fascia was cleared to expose bregma, then the incision was sutured closed. Sham surgeries were matched to lesion surgeries for all experimental conditions.

Progesterone Treatment.

Sham (S) and lesion (L) animals were randomly assigned to one of three treatment groups: vehicle (VS, VL), acute withdrawal (AWS, AWL), and tapered withdrawal (TWS, TWL). Sixteen mg/kg progesterone treatments were dissolved in 22.5% 2-hydroxypropyl-β-cyclodextrin (HBC) and administered as shown in Table 2. Tapering was induced as halved dosages over the last two days of treatment. Dilutions for TW treatments were made with HBC stock. All injections were administered intraperitoneally at one hour post-injury, and subcutaneously at six hours post-injury and every 24 hours through the end of the treatment cycle. Five sets of 12 animals each were used, for a total n=10 for each experimental group over the entire experiment. Of these animals, all were used to acquire behavioral data, four samples were used for protein analysis, and six samples were used for histological analysis for each test condition.

TABLE 2

Post-Surgery Progesterone Treatment Schedule
Progesterone Administration

| | Days 1-5 | Day 6 | Day 7 |
|---|---|---|---|
| AW | 16 mg/kg P | 16 mg/kg P | 16 mg/kg P |
| TW | 16 mg/kg P | 8 mg/kg P | 4 mg/kg P |
| V | 22.5% HBC | 22.5% HBC | 22.5% HBC |

Digiscan Locomotor Activity Boxes.

Random order, blinded testing occurred under red light in a quiet environment one day before injury, and one and seven days post-withdrawal. Up to four animals were tested using the Digiscan Activity Monitoring System (AccuScan Instruments, inc. Columbus, Ohio) in each trial, with a total of three trials per test day. Rats were placed in the furthest left corner of the Digiscan Activity Box. At that time, the toggle switch was flipped to 'on'. At exactly five minutes the computer ceased testing, assuring that all tests were the same length regardless of start time. Files were saved according to date and trial number, and the number of fecal boli recorded. Activity boxes were cleaned with 70% ethanol and dried between trials. Center time was defined by the computer as the amount of time the animal spent exploring the activity box away from the corners.

Somatosensory Neglect of the Forepaws.

Random order, blinded testing occurred under red light in a quiet environment at one and seven days post-withdrawal, one hour after locomoter activity testing. 1.3 cm diameter circular labels were placed on the left forepaw and the rat placed in the clear plexiglass testing box. The latency required for each rat to remove the sticker with its mouth was recorded, with maximum test duration of two minutes. Each animal was tested three times, with a rest period of two minutes between trials. The testing box was cleaned with 70% ethanol and dried between trials.

Tissue Preparation.

All animals were decapitated following a lethal 1 mL injection of Nembutal at three weeks post-injury. Brains for histological analysis were extracted after transcardial perfusion with 4% paraformaldehyde. After 24 hours of post-fixation in 4% paraformaldehyde, followed by 10% sucrose and then 20% sucrose solution in DI water, brains were mounted and frozen under dry ice. The forebrain was cut into 25 um sections on a cryostat and stored at −80° C. on 1% gelatin-coated slides. Evenly spaced sections 75 µm apart were washed in a graded alcohol series, 100% and 95% alcohol (2×5 min each) and 70% alcohol (1×5 min) and stained with thionin (1 g thionin, 1.2 g sodium acetate, 0.4 mL glacial acetic acid in 300 mL DI H20) for lesion reconstruction. Thionin-stained sections from 4.2-2.2 mm anterior to bregma were identified and analyzed for lesion area using Kodak ID software. Total brain area was determined by determined by normalizing to the volume of sham brain sections.

Brains for protein analysis were sectioned into the immediate area of the lesion and snap frozen in 2-methyl-butane chilled on dry ice. Samples were stored at −80° C. Brain sections were weighed to assure consistency and homogenized via a glass Dounce in 800 mL Tper homogenization buffer (78510, Pierce, Rockford, Ill.) with 10 µl/ml of protease inhibitor cocktail (P8340, Sigma, St. Louis, Mo.). Homogenized tissue samples were stored at −20° C. BCA and Coomassie protein assays (23235, Pierce) were performed in triplicate at three dilutions on each sample to determine protein concentration. The amount of brain homogenate needed to standardize samples to 2 μg/μL for Western blotting was calculated from the results of these assays.

Immunohistochemistry.

Sections used for GFAP immunofluorescence staining were rinsed in PBS, then incubated in 0.2% TritonX in PBS for 5-10 minutes and rinsed again. Sections were then incubated in 1.0% Bovine Serum Albumin (BSA) in PBS for 30 minutes, and left overnight at 4° C. under 1:2000 GFAP (MAB3402, Chemicon) in 1% BSA. After a rinse in PBS and a ten minute incubation in 1% BSA, sections were incubated in 1:1000 mouse-conjugated AlexaFluor 594 (A21125, Invitrogen, Carlsbad, Calif.) secondary antibody solution in 1% BSA overnight at 4° C. Slides were cover slipped using Vectashield Mounting Medium (H-1000, Vector Laboratories, Burlingame, Calif.). Slides were processed at 40× magnification with a Nikon Olympus microscope equipped with epifluorescence. Prior to acquiring and analyzing images, the microscope was calibrated to 1 μm. Four separate areas directly adjacent to the injury area were analyzed per section. Luminosity was quantified for n=6 per treatment group with Adobe Photoshop v. 6.0. For each 144 k+ pixel image, the rating is determined and averaged per pixel over the whole.

Western Blotting.

Reducing sample buffer was prepared as 0.625 M Tris, 10% Glycerol, 2% SDS, 5% β-mercaptoethanol and 0.001% Bromophenol Blue. Samples were set to 2 μg/μl protein concentration. Prepared samples were applied to 4-20% gradient TrisHCL gels (345-0033, Biorad, Hercules, Calif.), and run at 200 mV for approximately one hour. Proteins were then transferred onto PVDF membranes in the Criterion Western transfer module (165-6001, BioRad), blocked for several hours in milk protein diluent (50-82-00, KPL, Gaithersburg, Md.) and then incubated in primary antibody overnight at 4° C., including p53 (SC-1312, Santa Cruz Biotechnology, Santa Cruz, Calif.) BDNF (AB1534, Chemicon, Temecula, Calif.) and HSP70 (33-3800, Zymed, Carlsbad, Calif.). HRP-conjugated secondary antibodies (4-18-18, 14-13-06, KPL) were applied the following day for 2 hours and shaken at room temperature. Blots were developed with SuperSignal West Dura substrate (34076, Pierce) using a Kodak scanner and Kodak ID software for densitometry analysis. Loading controls were performed with β-actin housekeepers.

Statistics.

All results were expressed as the mean plus or minus the standard error of the mean. Statistical significance was set at $p<0.05$ for two-tailed tests, and data were analyzed using one-way analysis of variance (ANOVA) followed by LSD post hoc tests. F-values are presented as a preface to post-hoc analysis with all degrees of freedom for Western blotting at (5,18) and for behavior at (5,26). LSD results were used to demonstrate significance.

Results

Behavioral Assays.

Figure 3:
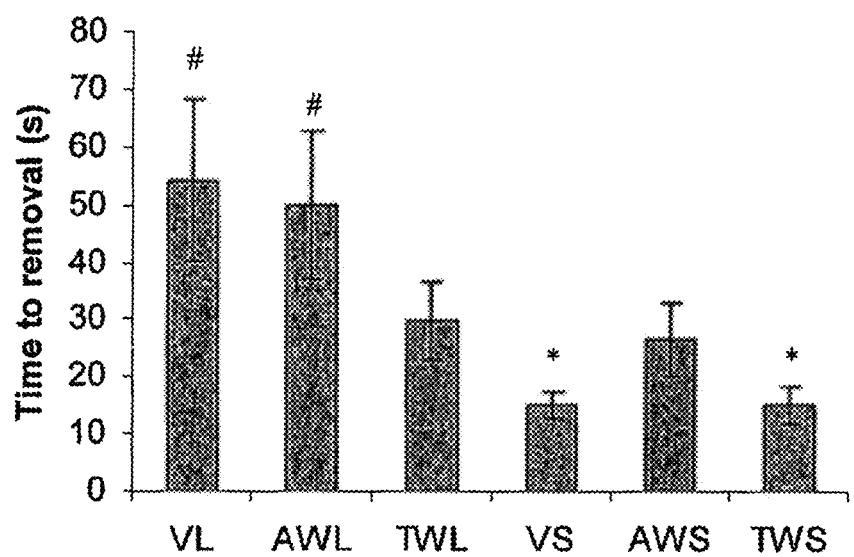
FIG. 3 shows somatosensory neglect data at one day (FIG. 3A) and one week (FIG. 3B) post-withdrawal.
Figure 3:
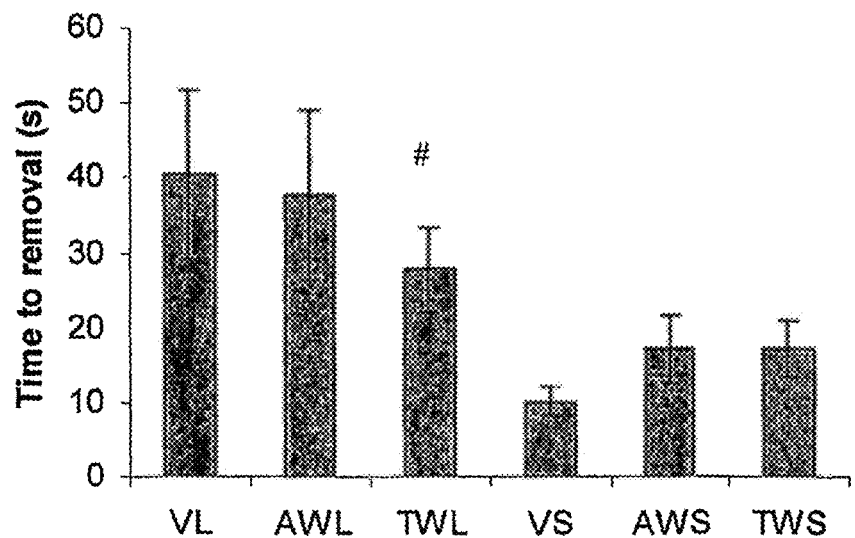

Somatosensory neglect data is shown at one day (FIG. 3A) and one week (FIG. 3B) post-withdrawal. At both time points, TWS and VS showed no differences. At one day post withdrawal, AWS demonstrated elevated sensory deficiencies compared to the TWS and VS groups (*, $p<0.05$, F=8.97), however, at one week post withdrawal these differences were no longer evident. At both time points, AWL and VL did not display differences, however, both decrease from one to seven days. TWL, however, remained the same over the course of the experiment, and deficiencies were decreased compared to VL and AWL (#, $p<0.05$, F=10.71, 8.85) at both times.

Figure 4:
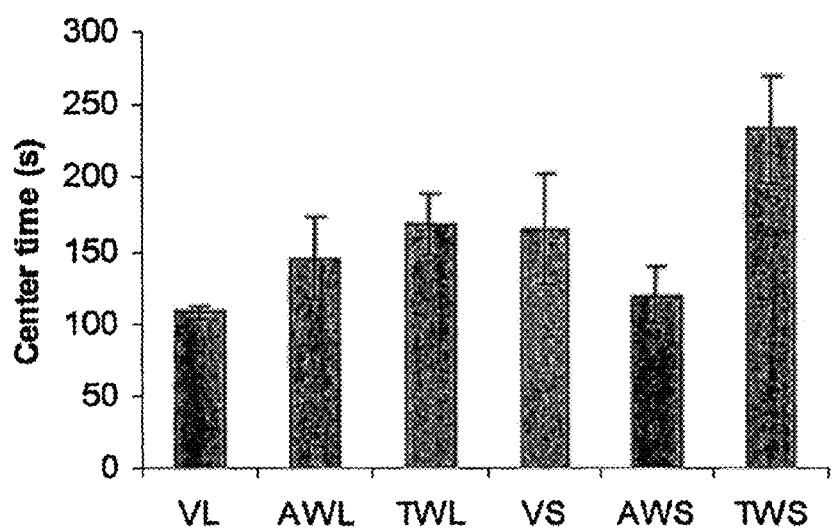
FIG. 4 shows center time, as determined from Digiscan Locomoter Activity Boxes, between one (FIG. 4A) and seven (FIG. 4B) days post-withdrawal.
Figure 4:
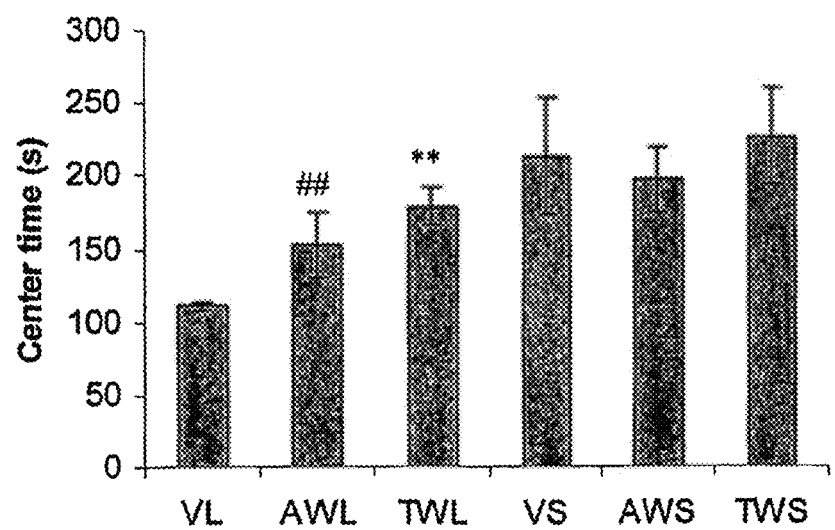

Center time, as determined from Digiscan Locomoter Activity Boxes, followed a similar pattern to that seen in the progression of sensory neglect between one (FIG. 4A) and seven (FIG. 4B) days post-withdrawal. At one day, AWS animals demonstrated significantly less center time compared to other shams (*, $p<0.05$, F=6.79); at seven days all sham animals spent equivalent center time. TWS animals did have increased center time at one day compared to VS animals (#, $p<0.05$, F=10.13). This indicated an anxiogenic effect of progesterone withdrawal beyond the peak of withdrawal. At both time points, TWL animals demonstrated increased center time over AWL animals (**, $p<0.05$, F=7.74, 5.33), which in turn had increased center time compared to VL animals (##, $p<0.05$, F=8.91, 10.77).

Protein Analysis.

Figure 5:
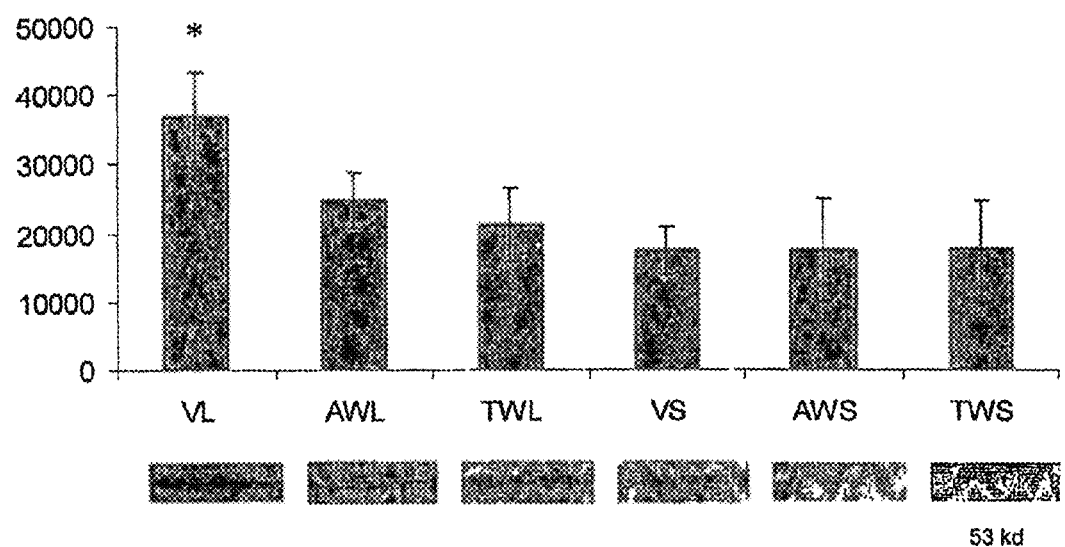
FIG. 5 shows p53 Western blotting densitometry between experimental groups demonstrating an increase in apoptotic activity for VL animals over all other treatment groups (*, $p<0.05$).
Figure 6:
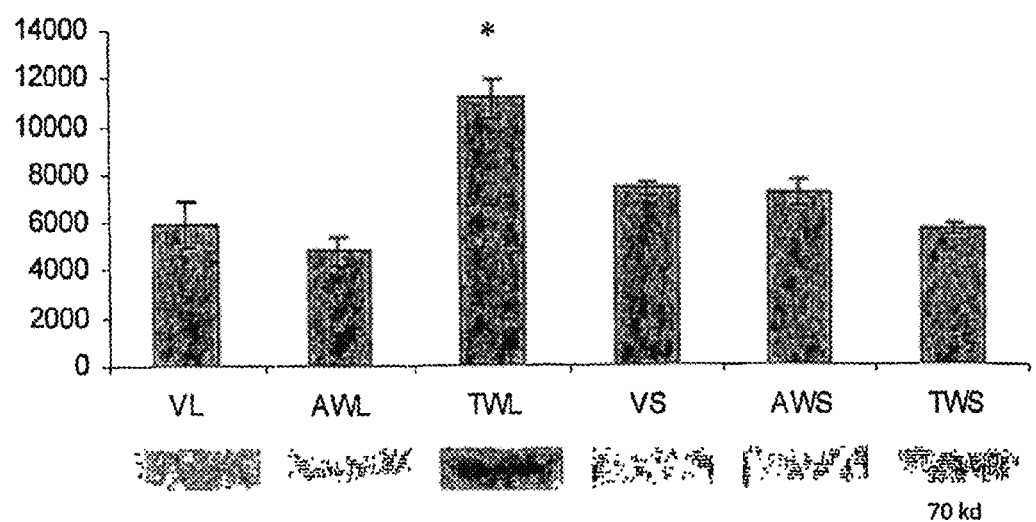
FIG. 6 shows HSP70 Western blotting densitometry between experimental groups demonstrating an increase for TWL animals over all other groups (*, $p<0.05$).

FIG. 5 shows p53, a long-term marker of apoptosis. At two weeks post-withdrawal, all progesterone-treated animals had p53 levels indistinguishable from vehicle shams. VL animals, however, had significantly higher p53 levels than all other groups (*, $p<0.05$, F=8.67). HSP70, a neuroprotective protein, was increased in TWL animals (*, $p<0.05$, F=26.94) over both VL and AWL (FIG. 6). Sham animals did not display any differences between treatment groups.

Figure 7:
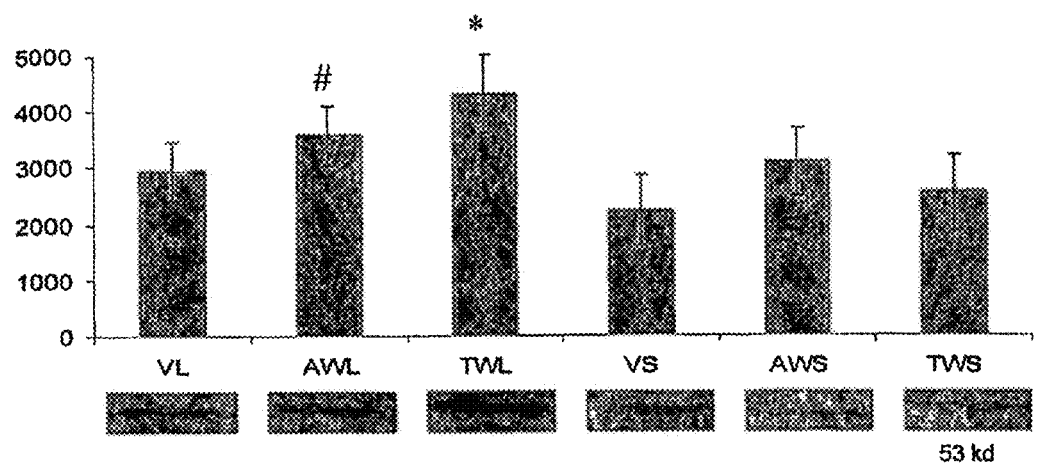
FIG. 7 shows BDNF Western blot densitometry between experimental groups demonstrating an increase for TWL animals over all other groups (*, $p<0.05$), followed by AWL (#, $p<0.05$). VL BDNF levels were comparable to shams.

FIG. 7 demonstrates an increase in BDNF levels for TWL over AWL (*, $p<0.05$, F=6.88) and AWL over VL (#, $p<0.05$, F=6.57). Sham animals did not display any differences between treatment groups. Coupled with HSP70 data, this indicates that the neuroprotective properties of progesterone are enhanced with a tapered treatment regime.

Histology.

Figure 8:
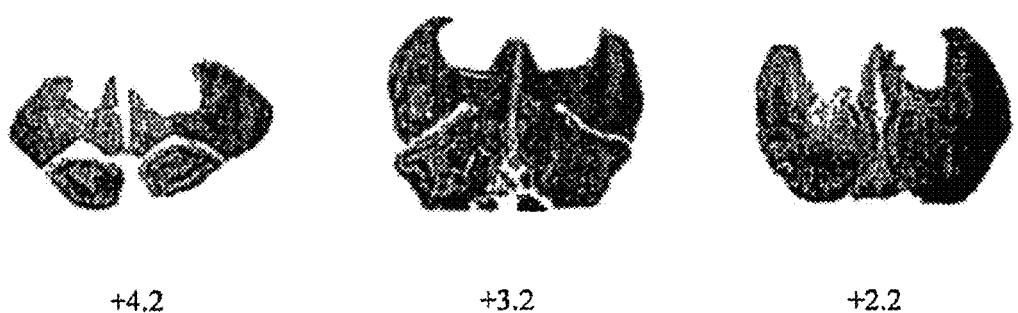
FIG. 8 shows representative images of selected sections anterior to bregma (FIG. 8A), and quantified data for each lesion group (FIG. 8B).
Figure 8:
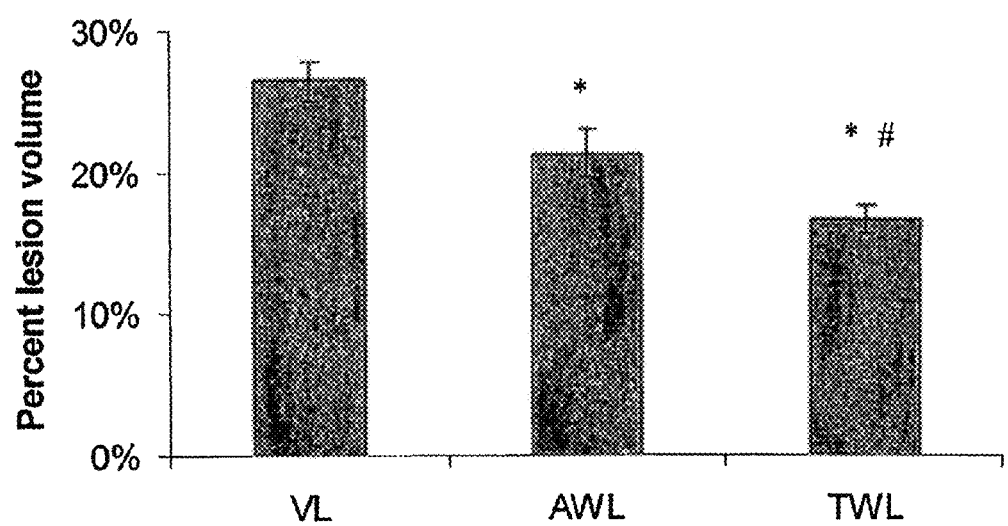

Lesion reconstruction was performed at +2.2, +3.2, and +4.2 mm from bregma. The ratio of lesion volume to total volume was determined for an n=4 for each depth. FIG. 8A shows representative images of the selected sections anterior to bregma, and the quantified data for each lesion group is shown in FIG. 8B. TWL brains had a smaller lesion volume than AWL and VL animals (*, #, $p<0.05$, F=7.32), while AWL lesion volume was decreased compared to VL animals (*, $p<0.05$, F=4.55).

Figure 9:
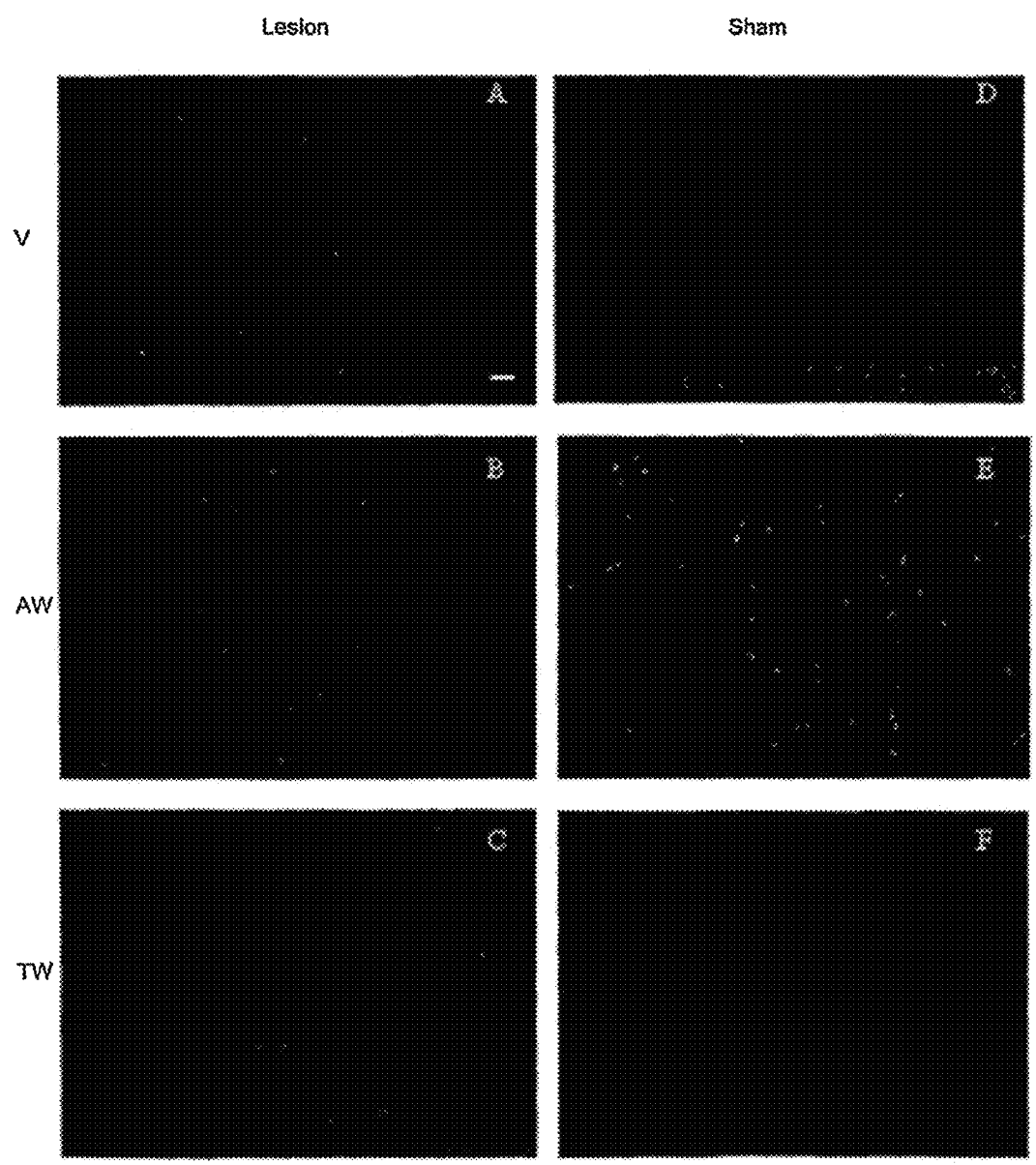
FIG. 9 and FIG. 10 show relative reactive astrocytes as determined by immunofluorescent GFAP staining at three weeks post-injury.
Figure 10:
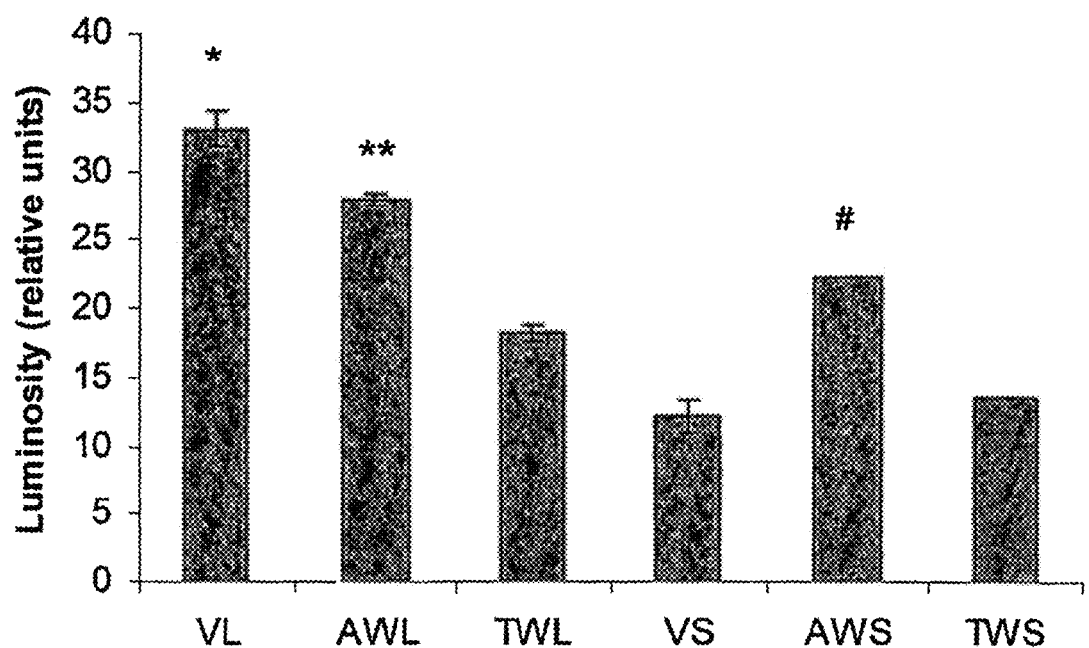

FIG. 9 and FIG. 10 demonstrate relative reactive astrocytes as determined by immunofluorescent GFAP staining at three weeks post-injury. FIG. 9 shows representative views from each group at the lesion site or the corresponding tissue in sham animals while FIG. 10 shows the quantified luminosity averaged over n=6. GFAP was upregulated in VL (A) animals over AWL (B) animals, and in AWL compared to TWL (C) animals (*, $p<0.05$, F=16.24, 27.96). AWS (E) animals had an increase in GFAP reactivity over both VS (D) and TWS (F) groups (#, $p<0.05$, F=9.71). TWS and VS groups did not display differences.

Discussion

This study investigated the effects of acute progesterone withdrawal three weeks after injury, and found selective long-term repercussions. Several measures of long-term behavioral, anatomical, and molecular functions were investigated to indicate recovery of activity, sensory and cellular response.

In order to determine long-term behavioral responses to acute versus tapered progesterone withdrawal, locomotor activity and somatosensory neglect tests were performed. Animals with tapered withdrawal from progesterone performed better one day and one week post-withdrawal for both sensory recovery of function and locomotor activity. Additionally, at one day post-withdrawal, sham-operated animals that underwent acute progesterone withdrawal demonstrated more deficiencies in these assays than tapered or vehicle sham animals; this effect disappeared one week later. An interesting observation immediately post-withdrawal was an increase in the time spent in the center of the activity box for tapered shams over vehicle shams. This increased exploratory behavior may be due to a mild excitatory effect from the gradual withdrawal, in contrast to the more severe excitotoxic, and limiting effect of the acute withdrawal. In addition, mild excitation may further enhance long term recovery of function, as delayed exercise after TBI improves function recovery (Griesbach et al. (2004) *Neuroscience*, 125:129-139; Kleim et al. (2003) *Neurochem. Res.*, 28:1757-1769; Will et al. (2004) *Prog. Neurobiol.*, 72:167-182).

Selective effects of acute versus tapered PW were also seen in terms of molecular analyses three weeks after injury. While apoptosis was increased for acute compared to tapered PW at the time of withdrawal (Cutler et al. (2005) *Exp. Neurol.*, 195:423-429), this effect was no longer evident two weeks later as determined by p53 protein levels. Vehicle-treated animals, however, did maintain elevated apoptosis compared to progesterone treatments.

A greater long-term consequence of acute withdrawal was seen in terms of neuroprotection. BDNF and HSP 70, both indicators of neuroprotection, were increased for tapered compared to acute withdrawal, while all progesterone treatment resulted in increased HSP70 compared to vehicle-treated animals. Specifically, BDNF acts to protect tissue from insult and enable post-trauma neuronal plasticity through various mechanisms (Binder and Scharfman (2004) *Growth Factors*, 22:123-131; Chuang (2004) *Crit. Rev. Neurobiol.*, 16:83-90; Gonzalez et al. (2004) *Neuroscience*, 125:605-614), while HSP 70 acts as a neuroprotective agent by suppressing inflammatory responses and cytotoxicity (Feinstein et al. (1996) *J. Biol. Chem.*, 271:17724-17732). Taken together, the present molecular findings and the decreased necrotic lesion volume for tapered over acute progesterone over vehicle treatment, demonstrated an overall picture of enhanced neuroprotection and neuroplasticity with tapered progesterone administration.

Immunofluorescent staining for GFAP indicated the extent of astrocyte reactivity adjacent to the injury site. While an increase in GFAP can be a hallmark of increased trophic factors, it also indicates glial scarring, inflammation, and cerebral edema (Hatten et al. (1991) *Glia*, 4:233-243; Leme and Chadi (2001) *Arq. Neuropsiquiatr.*, 59:483-492). As predicted, in the present study an increased response for vehicle-treated lesion animals and a decreased GFAP reaction for acute progesterone-treated lesion animals was observed. The GFAP response was further decreased for tapered progesterone-treated lesion animals.

It should also be noted that an increase in the luminosity of GFAP immunofluorescence was found in the acute PW sham group. Without being bound by theory, the mechanism of sham response may be based solely on effects stemming from acute PW. After acute progesterone withdrawal, increased action of the NMDA and sigma receptors creates an environment of neural excitation. The degree of this excitation is dependent on several factors, including dosage and duration of administration (Rupprecht et al. (2001) *Brain Res. Brain Res. Rev.*, 37:59-67; Rupprecht and Holsboer (2001) *Int. Rev. Neurobiol.* 46:461-477), and may also be compounded by external events such as trauma. Accordingly, an effect of recovery from an excitotoxic environment could be increased trophic factor release (Acarin et al. (1999) *J. Neuropathol. Exp. Neurol.*, 58:389-397; Horvath et al. (2000) *Eur. J. Pharmacol.* 405:33-42), as observed in acute PW sham animals.

These combined molecular and immunohistological data support the previous findings described above (see Experiment 3; Cutler et al. (2005) *Exp. Neurol.*, 195(2):423-429), showing that while progesterone can be a vital therapeutic treatment, its beneficial effects are further enhanced by reducing the secondary complications attributable to acute PW. The clinical implications of these findings hold promise for designing an effective response to both the immediate and long-term rehabilitative requirements after TBI. In order to optimize treatment and promote all stages of functional recovery, the current study could be applied to encompass post-trauma rehabilitation, including the effects of exercise and enriched environments (Griesbach et al. (2004) *Neuroscience*, 125:129-139; Kempermann et al. (2000) *Prog. Brain Res.*, 127:35-48; Will et al. (2004) *Prog. Neurobiol.*, 72:167-182). Also, while young adults are the largest demographic for TBI, both immature and elderly patients contribute significantly to TBI statistics through shaken baby syndrome, accidents, and falls (CDC, 2004) and may also benefit from such therapeutic strategies.

In conclusion, both long and short-term indices of recovery are enhanced with tapered progesterone treatment. This knowledge opens the door to more effective design, research, and implementation of a safe and effective clinical treatment for TBI.

SUMMARY

Adult, male Sprague-Dawley rats received either bilateral frontal cortex contusion (L) or sham (S) surgery. Rats were injected at one and six hours post injury, then every 24 hours for six days. Vehicle (V) treated rats were given 9 injections of 22.5% cyclodextrin, while AW rats received 9 injections of 16 mg/kg progesterone and TW rats received 7 injections of progesterone at 16 mg/kg, followed by one at 8 mg/kg and one at 4 mg/kg. On day 8, sensory neglect and locomotor activity tests were initiated. Animals were killed 22 days post-TBI and the brains prepared for either molecular or histological analysis. Western blotting revealed increased BDNF and HSP 70 in TW vs. AW animals. P53 was increased in VL animals, while all progesterone-treated groups were equivalent to shams. TW animals had markedly decreased sensory neglect compared to AW animals, and increased center time in locomotor activity assays. In addition, lesion reconstruction revealed a decreased lesion size for TWL over AWL over VL animals. GFAP immunofluorescent staining followed this pattern as well. In conclusion, after TBI, AW affects select behaviors and molecular markers in the chronic recovery period.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of treating a traumatic brain injury, said method comprising administering a therapeutically effective amount of progesterone to a subject in need thereof, wherein prior to termination of administration of progesterone, said administration comprises a tapered administration dosing regimen.

2. The method of claim 1, wherein said traumatic brain injury results from a blunt force contusion.

3. The method of claim 1, wherein said tapered administration dosing regimen comprises progressively administering 50% divided doses of progesterone.

4. The method of claim 1, wherein said tapered administration dosing regimen comprises a linear taper.

5. The method of claim 4, wherein said linear taper is a 10% linear taper.

6. The method of claim 1, wherein said tapered administration dosing regimen comprises an exponential taper.

7. The method of claim 1, wherein said tapered administration dosing regimen is used in combination with administration of progesterone at least once a day.

8. The method of claim 1, wherein said therapeutically effective amount of progesterone administered to said subject prior to the tapered administration dosing regimen comprises a constant progesterone dosing regimen.

9. The method of claim 1, wherein said therapeutically effective amount of progesterone administered to said subject prior to the tapered administration dosing regimen comprises a two-level progesterone dosing regimen.

10. The method of claim 1, wherein said tapered administration dosing regimen is carried out over a period of about 24 hours.

11. The method of claim 1, wherein said tapered administration dosing regimen is carried out over a period of about 48 hours.

12. The method of claim 1, wherein said tapered administration dosing regimen comprises a series of tapered doses.

13. The method of claim 4, wherein said linear taper is a 25% linear taper.

14. The method of claim 4, wherein said linear taper is a 50% linear taper.

15. The method of claim 1, wherein said tapered administration is effected over a period of about 24 hours and comprises a series of doses tapered at a 25% linear taper.

16. The method of claim 1, wherein the pharmaceutical composition is administered by a route selected from the group consisting of oral, vaginal, rectal, topical, nasal, ophthalmic, and parenteral.

17. The method of claim 16, wherein the pharmaceutical composition is administered by a route selected from the group consisting of systemic, intraperitoneal, intravenous (IV), intramuscular (IM), subcutaneous (SC), transdermal, buccal, and intracerebroventricular.

18. The method of claim 16, wherein the pharmaceutical composition is in a form selected from the group consisting of a solid, a particulant, a powder, a solution, a suspension, and an emulsion.

\* \* \* \* \*

UNITED STATES PATENT AND TRADEMARK OFFICE
CERTIFICATE OF CORRECTION

PATENT NO. : 8,614,203 B2
APPLICATION NO. : 13/550148
DATED : December 24, 2013
INVENTOR(S) : Donald G Stein et al.

It is certified that error appears in the above-identified patent and that said Letters Patent is hereby corrected as shown below:

In the Specification

Column 1, line 16, please delete

"This invention was made with United States Government support under grant numbers R01 N5038664-04 and R01-N5040825 awarded by the National Institute of Neurological Disorders and Stroke (NINDS) of the National Institutes of Health. The United States Government has certain rights in this invention."

and insert the following:

-- This invention was made with government support under grant numbers R01 N5038664-04 and R01-N5040825 awarded by the National Institute of Neurological Disorders and Stroke (NINDS) of the National Institutes of Health. The government has certain rights in this invention. --

Signed and Sealed this
Third Day of June, 2014

Michelle K. Lee
*Deputy Director of the United States Patent and Trademark Office*